(12) United States Patent
Urakawa et al.

(10) Patent No.: US 12,085,527 B2
(45) Date of Patent: Sep. 10, 2024

(54) CELL POTENTIAL MEASUREMENT DEVICE

(71) Applicant: SCREEN HOLDINGS CO., LTD., Kyoto (JP)

(72) Inventors: Satoshi Urakawa, Kyoto (JP); Masakazu Sanada, Kyoto (JP)

(73) Assignee: SCREEN HOLDINGS CO., LTD., Kyoto (JP)

( * ) Notice: Subject to any disclaimer, the term of this patent is extended or adjusted under 35 U.S.C. 154(b) by 24 days.

(21) Appl. No.: 17/618,720

(22) PCT Filed: Jun. 22, 2020

(86) PCT No.: PCT/JP2020/024335
§ 371 (c)(1),
(2) Date: Dec. 13, 2021

(87) PCT Pub. No.: WO2020/262285
PCT Pub. Date: Dec. 30, 2020

(65) Prior Publication Data
US 2022/0244210 A1     Aug. 4, 2022

(30) Foreign Application Priority Data

Jun. 25, 2019 (JP) .................................. 2019-116912

(51) Int. Cl.
*G01N 27/22* (2006.01)

(52) U.S. Cl.
CPC ......... *G01N 27/227* (2013.01); *G01N 27/226* (2013.01)

(58) Field of Classification Search
CPC .. G01N 27/227; G01N 27/226; G01N 27/416; G01N 27/26; G01N 27/3275; C12M 41/46; C12M 35/02
See application file for complete search history.

(56) References Cited

U.S. PATENT DOCUMENTS

| | | | |
|---|---|---|---|
| 2002/0063067 A1 | 5/2002 | Bech et al. | |
| 2002/0113607 A1 | 8/2002 | Yukimasa | |

(Continued)

FOREIGN PATENT DOCUMENTS

| | | |
|---|---|---|
| CN | 1383487 A | 12/2002 |
| CN | 101517403 A | 8/2009 |

(Continued)

OTHER PUBLICATIONS

Abe, "A Contamination-Free Microstructure in a Humid Environment by Means of a Combination of Hydrophilic and Hydrophobic Surfaces" (Year: 1998).*

(Continued)

*Primary Examiner* — Feba Pothen
(74) *Attorney, Agent, or Firm* — Rimon P.C.

(57) ABSTRACT

A cell potential measurement device has a measuring plane on which a cell suspension is dropped. The cell potential measurement device includes a plurality of working electrodes and a reference electrode. The plurality of working electrodes are two-dimensionally arranged in a working region of the measuring plane. The reference electrode is provided outside the working area of the measuring plane. A contact angle in a hydrophobic region between the working region and the reference electrodes of the measuring plane is larger than a contact angle in the working region.

9 Claims, 21 Drawing Sheets

(56) References Cited

U.S. PATENT DOCUMENTS

| | | |
|---|---|---|
| 2003/0194709 A1 | 10/2003 | Yang |
| 2005/0002985 A1 | 1/2005 | Heal et al. |
| 2005/0069458 A1 | 3/2005 | Hodes et al. |
| 2005/0237065 A1 | 10/2005 | Kudoh et al. |
| 2009/0152517 A1 | 6/2009 | Takiguchi et al. |
| 2009/0246279 A1 | 10/2009 | Kong et al. |
| 2010/0116682 A1 | 5/2010 | Neuzil et al. |
| 2011/0033515 A1 | 2/2011 | Harpstead et al. |
| 2012/0276334 A1 | 11/2012 | Fedynyshyn et al. |
| 2013/0116128 A1 | 5/2013 | Shen et al. |
| 2013/0252932 A1 | 9/2013 | Seward |
| 2014/0199719 A1 | 7/2014 | Shih et al. |
| 2015/0014160 A1 | 1/2015 | Hyde et al. |
| 2016/0289669 A1 | 10/2016 | Fan et al. |
| 2018/0104686 A1 | 4/2018 | Watanabe et al. |
| 2018/0250672 A1 | 9/2018 | Jamshidi et al. |

FOREIGN PATENT DOCUMENTS

| | | |
|---|---|---|
| CN | 104467515 A | 3/2015 |
| CN | 107709223 A | 2/2018 |
| CN | 107748261 A | 3/2018 |
| CN | 208705263 U | 4/2019 |
| JP | H09-210955 A | 8/1997 |
| JP | H09-274925 A | 10/1997 |
| JP | 11-187865 A | 7/1999 |
| JP | 2000-67874 A | 3/2000 |
| JP | 2002-031617 A | 1/2002 |
| JP | 2002-523726 A | 7/2002 |
| JP | 2003/511668 A | 3/2003 |
| JP | 2004-510980 A | 4/2004 |
| JP | 2004-233301 A | 8/2004 |
| JP | 2005/233641 A | 9/2005 |
| JP | 2009-245782 A | 10/2009 |
| KR | 10-2017-0114754 A | 10/2017 |
| WO | 99/034202 A1 | 7/1999 |
| WO | 01/025769 A2 | 4/2001 |
| WO | 02/029402 A2 | 4/2002 |

OTHER PUBLICATIONS

International Search Report issued in corresponding International Patent Application No. PCT/JP2020/024335, dated Sep. 1, 2020, with English translation.
Japanese Notice of Reasons for Refusal issued in corresponding Japanese Patent Application No. 2019-116912, dated Aug. 9, 2022, with English translation.
Transmittal of International Preliminary Report on Patentability and Written Opinion of the International Searching Authority for PCT/JP2020/024335, dated Dec. 28, 2021 with English translation.
Extended European Search Report dated Jun. 14, 2023 for EP Application No. 20832065.5.
He Ziyi, "Development of cell analysis platforms based on DNA-mediated cell surface engineering and microfluidic chips", «Chinese outstanding doctoral theses entire database of Basic Science» Tsinghua University, Apr. 2017, w/ English Abstract.
Wu Changyu, "Spectroscopic and electrochemical studies on interactions of the bio-molecular probes with cancer cells", «Chinese outstanding doctoral theses entire database of Medical and Health Technology» School of Biological Science and Medical Engineering, southeast University, Mar. 4, 2016, w/ English Abstract.
Park, HM, "Zeta Potential and Slip Coefficient Measurements of Hydrophobic Polymer Surfaces Exploiting a Microchannel", «Industrial & Engineering Chemistry Research» Apr. 12, 2012, ACS Publications, vol. 51, Season 19.
P.I. Peterkin, E.S. Idziak, A.N. Sharpe, "Screening DNA probes using the hydrophobic grid-membrane filter", Food Microbiology, vol. 6, Issue 4, 1989, pp. 281-284.
Office Action issued in the corresponding Chinese patent Application No. 202080047863.8 dated Mar. 21, 2024.

\* cited by examiner

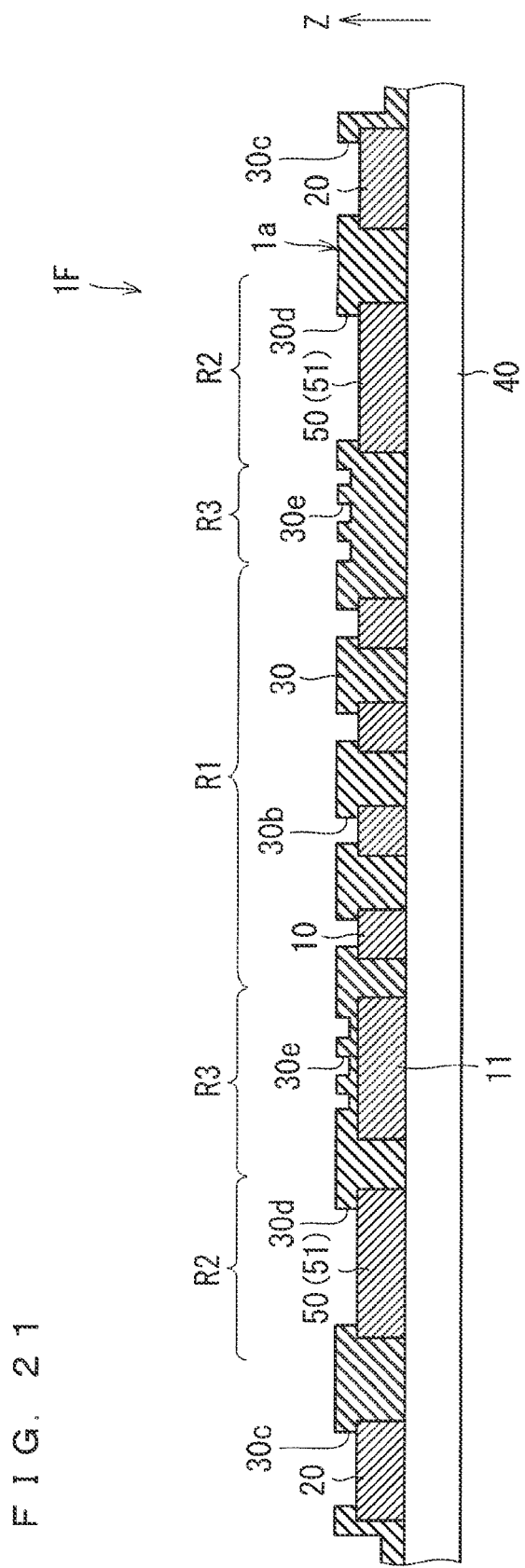
F I G. 21

CELL POTENTIAL MEASUREMENT DEVICE

CROSS REFERENCE TO RELATED APPLICATIONS

This application is the U.S. National Phase under 35 U.S.C. § 371 of International Application No. PCT/JP2020/024335, filed on Jun. 22, 2020, which claims the benefit of Japanese Application No. 2019-116912, filed on Jun. 25, 2019, the entire contents of each are hereby incorporated by reference.

TECHNICAL FIELD

The present application relates to a cell potential measurement device.

BACKGROUND ART

Conventionally, a cell potential measurement device that measures an induced potential of cells or tissues of nerve cells or the like has been proposed (for example, Patent Document 1). In Patent Document 1, the cell potential measurement device includes an electrode assembly, and a plurality of microelectrodes and reference electrodes are provided on the surface of the electrode assembly (hereinafter, referred to as a measuring plane). The plurality of microelectrodes are arranged in a matrix in a rectangular region in the measuring plane. The reference electrodes are provided on the extended lines of the diagonal lines of the rectangular region.

At the time of measurement, an operator drops a liquid (which may also be called a cell suspension) such as a culture solution containing a cell or tissue section onto the measuring plane. Specifically, the operator drops the liquid onto the measuring plane in a manner that the liquid covers the rectangular region and does not come into contact with any the reference electrode. Then, by leaving the electrode assembly in this state, the cell or tissue section in the liquid is deposited on the rectangular region of the measuring plane to form a layer (hereinafter referred to as a cell layer). Accordingly, the microelectrodes detect the potential of cells or tissues in the cell layer. On the other hand, no section is present on the reference electrodes. The cell potential measurement device measures the difference between the potential detected by each microelectrode and the reference potential detected by the reference electrodes as an induced potential.

PRIOR ART DOCUMENTS

Patent Documents

[Patent Document 1] Japanese Unexamined Patent Application Publication No. 2002-523726

SUMMARY

Problem to be Solved by the Invention

In Patent Document 1, when the measuring plane on the electrode assembly is hydrophilic, the liquid spreads relatively thinly in plan view. Accordingly, the cell or tissue section is deposited in a wide range, the density of the cell layer formed on the measuring plane in plan view is small. More specifically, regions with low cell layer density can be unevenly distributed in plan view. When the density of the cell layer on the microelectrodes is low, the microelectrodes fail to measure the potential properly.

Therefore, an object of the present application is to provide a cell potential measurement device capable of improving the density of the cell layer formed on the measuring plane in plan view.

Means to Solve the Problem

The first aspect of the cell potential measurement device is a cell potential measurement device having a measuring plane on which a cell suspension is dropped, the potential measurement device including a plurality of working electrodes two-dimensionally arranged in a working region of the measuring plane, and a reference electrode provided outside from the working region of the measuring plane, in which, a contact angle in a hydrophobic region between the working region and the reference electrode of the measuring plane is larger than a contact angle in the working region.

The second aspect of the cell potential measurement device is the cell potential measurement device according to the first aspect, in which the hydrophobic region has an annular shape surrounding the working region.

The third aspect of the cell potential measurement device is the cell potential measurement device according to the first or second aspect, including a plurality of wires each drawn from corresponding one of the plurality of working electrodes and the reference electrode and extending outside the hydrophobic region, an insulating film covering the plurality of wires, and a hydrophobic film provided in the hydrophobic region and in which a contact angle is larger than a contact angle in the insulating film.

The fourth aspect of the cell potential measurement device is the cell potential measurement device according to the third aspect, in which the hydrophobic film is a conductive film.

The fifth aspect of the cell potential measurement device is the cell potential measurement device according to the fourth aspect, in which the conductive film is formed of a same material as at least any one of that of the plurality of working electrodes or the reference electrode and provided in a same layer as the plurality of working electrodes and the reference electrode so as to be insulated from the plurality of working electrode and the reference electrode.

The sixth aspect of the cell potential measurement device is the cell potential measurement device according to at least any one of the third to fifth aspects, in which the hydrophobic film has a concavo-convex shape for hydrophobization.

The seventh aspect of the cell potential measurement device is the cell potential measurement device according to the sixth aspect, in which the hydrophobic film has the concavo-convex shape in a radial cross section about a center of the working region.

The eighth aspect of the cell potential measurement device is the cell potential measurement device according to the first or second aspect, the cell potential measurement device further including a plurality of wires each drawn from corresponding one of the plurality of working electrodes and the reference electrode and extending outside the hydrophobic region, and an insulating film covering the plurality of wires, in which, in the hydrophobic region, the insulating film has a concavo-convex shape for hydrophobization.

The ninth aspect of the cell potential measurement device is the cell potential measurement device according to the first or second aspect, in which a contact angle in a hydrophilic region located between the working region and the hydrophobic region and surrounding the working region of the measuring plane is smaller than the contact angle in the working region.

The tenth aspect of the cell potential measurement device is the cell potential measurement device according to the ninth aspect, further including a plurality of wires each drawn from corresponding one of the plurality of working electrodes and the reference electrode and extending outside the hydrophobic region, an insulating film covering the plurality of wires and formed of a hydrophilic material, and a hydrophobic film provided in the hydrophobic region and in which a contact angle is larger than a contact angle in the insulating film, in which in the hydrophilic region, the insulating film has a concavo-convex shape for hydrophilicity.

The eleventh aspect of the cell potential measurement device is the cell potential measurement device according to the eighth or tenth aspect, in which the insulating film has the concavo-convex shape in regions avoiding directly above the plurality of wires.

The twelfth aspect of the cell potential measurement device is the cell potential measurement device according to at least any one of the eighth, tenth and eleventh aspects, in which the insulating film has the concavo-convex shape in a radial cross section about a center of the working region.

Effects of the Invention

According to the first aspect of the cell potential measurement device, the cell suspension is less likely to spread on the measuring surface. Consequently, improvement in the density of a cell layer formed on the measuring plane in plan view is ensured.

According to the second aspect of the cell potential measurement device, the spread of the cell suspension on the measuring plane can be controlled in a more isotropic manner.

According to the third aspect of the cell potential measurement device, the hydrophobic film can improve the contact angle in the hydrophobic region. Therefore, the material of the insulating film can be selected regardless of the contact angle in the hydrophobic region.

According to the fourth aspect of the cell potential measurement device, enlarging the contact angle in the hydrophobic region is ensured.

According to the fifth aspect of the cell potential measurement device, the metal film can be formed at the same time as the working electrodes or the reference electrode are formed. This makes the manufacturing of the cell potential measurement device facilitated and the cost thereof is reduced.

According to the sixth and seventh aspects of the cell potential measurement device, enlarging the contact angle further in the hydrophobic region is ensured.

According to the eighth aspect of the cell potential measurement device, enlarging the contact angle in the hydrophobic region is ensured.

According to the ninth aspect of the cell potential measuring device, even if the droplet position of the cell suspension deviates from the center of the working region, the cell suspension is prone to spreading circumferentially along the hydrophilic region; therefore the droplet is prone to covering the entire working region.

According to the tenth and eleventh aspects of the cell potential measurement device, while the hydrophobic film makes the contact angle large in the hydrophobic region, the concavo-convex shape of the insulating film makes the contact angle small in the hydrophilic region.

According to the twelfth aspect of the cell potential measurement device, the film thickness of the insulating film directly above the wires is made uniform and the wires are protected uniformly.

The objects, characteristics, aspects, and advantages of the technique disclosed in the present specification will become more apparent from the following detailed description and the accompanying drawings.

BRIEF DESCRIPTION OF DRAWINGS

FIG. 21 A plan view schematically illustrating the other configuration example of the cell potential measurement device.

DESCRIPTION OF EMBODIMENTS

Figure 1:
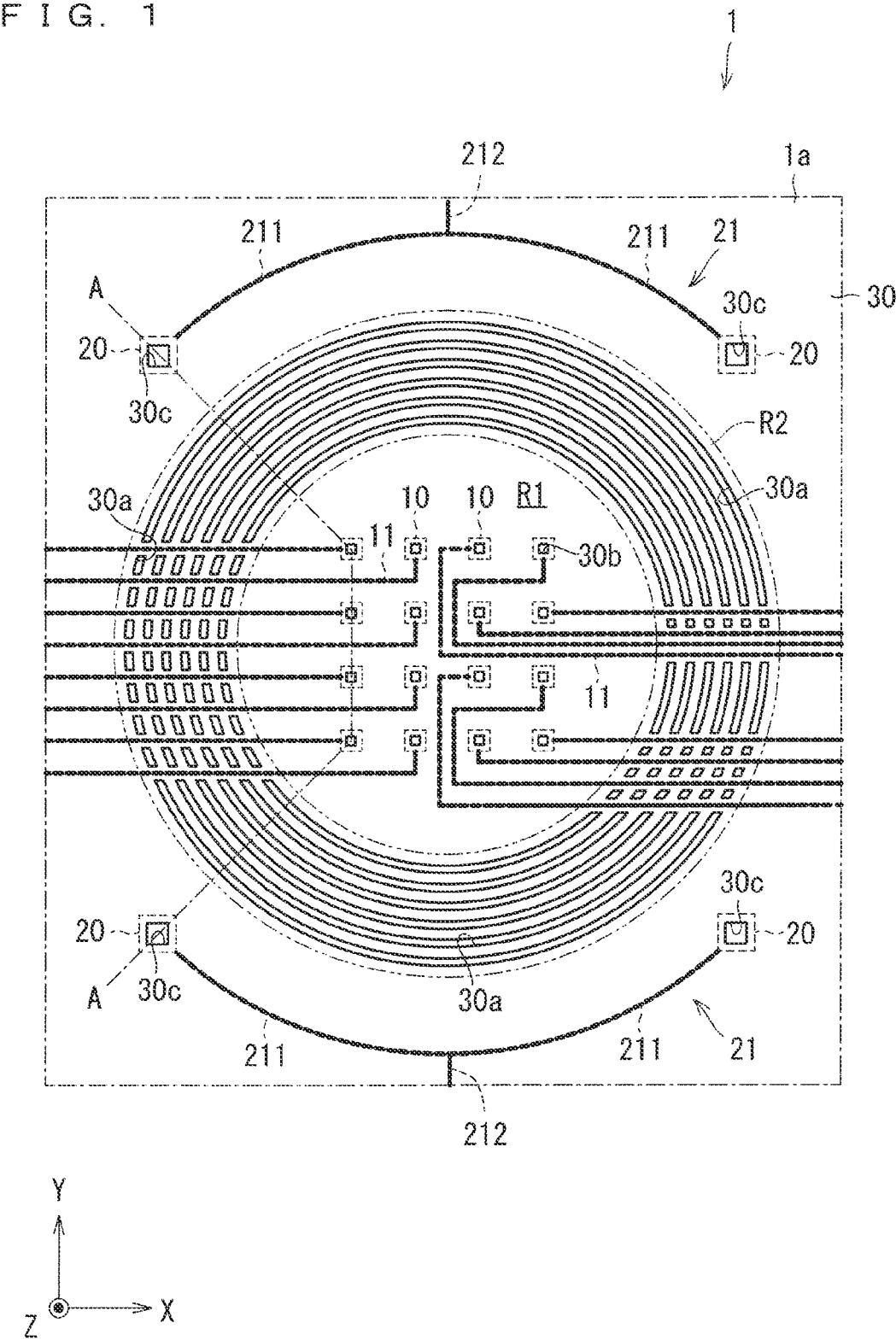
FIG. 1 A plan view schematically illustrating a configuration example of a cell potential measurement device.

Hereinafter, Embodiments will be described with reference to the attached drawings. It should be noted that the drawings are schematically illustrated and, therefore, the configurations are appropriately omitted or simplified in the drawings for facilitating the description. Also, the mutual relationship among sizes and positions in configurations and the like illustrated in the drawings are not necessarily accurately drawn, and may be changed as appropriate.

In addition, in the following description, the same components are denoted by the same reference numerals, and the names and functions thereof are also similar. Accordingly, detailed descriptions thereof may be omitted to avoid redundancy.

Further, in the drawings, XYZ orthogonal coordinate axes are appropriately attached. In the following, +X side represents one side in the X-axis direction, and −X side represents an other side in the X-axis direction. The same applies to the Y-axis direction and the Z-axis direction.

Embodiment 1

<Cell Potential Measurement Device>

Figure 2:
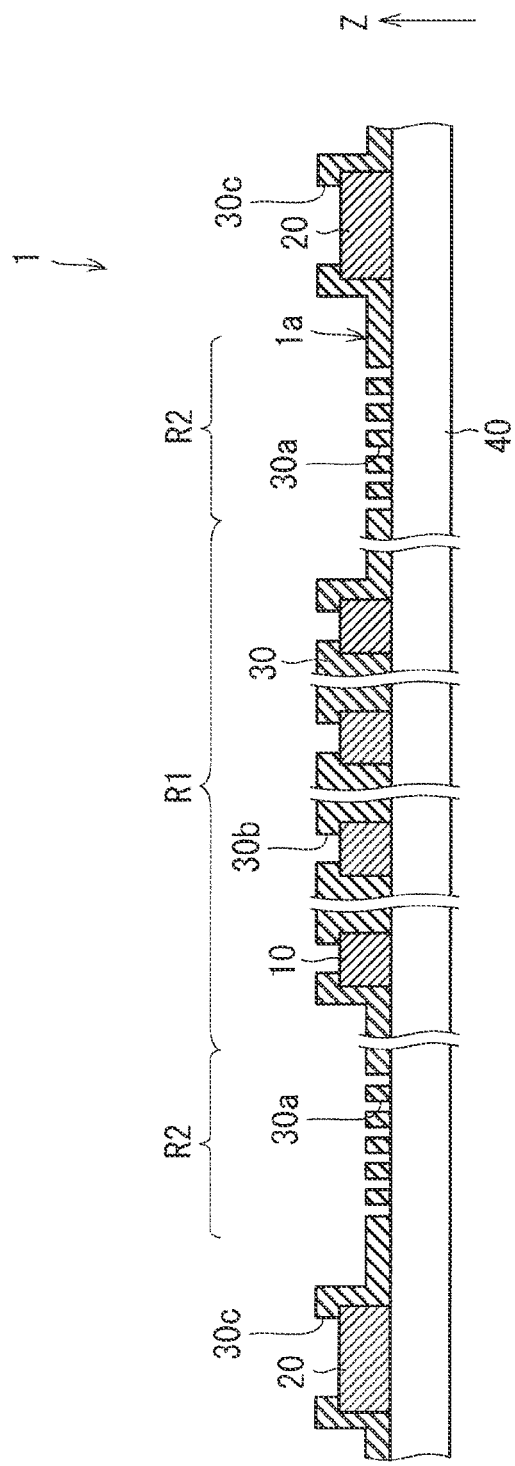
FIG. 2 A cross-sectional view schematically illustrating the configuration example of the cell potential measurement device.

FIG. 1 is a plan view schematically illustrating a configuration example of a cell potential measurement device 1, and FIG. 2 is a cross-sectional view schematically illustrating the configuration example of the cell potential measurement device 1. FIG. 2 schematically illustrates the configuration example of in the A-A cross section of FIG. 1. In the following, XYZ orthogonal coordinates will be introduced in order to explain the configuration of the cell potential measurement device 1. The Z-axis direction is the normal direction of a measuring plane 1a of the cell potential measurement device 1.

Figure 3:
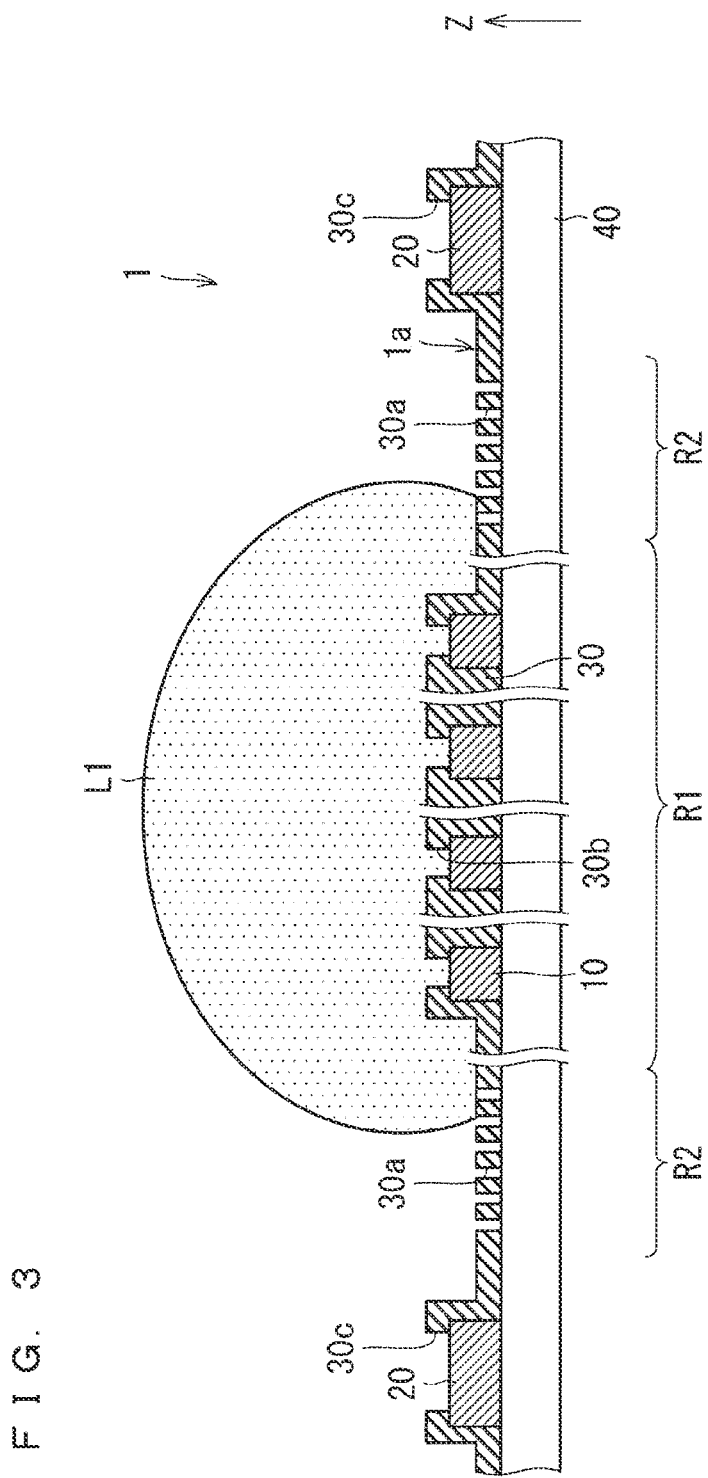
FIG. 3 A cross-sectional view schematically illustrating the configuration example of the cell potential measurement device in a state where a cell suspension is dropped.

The cell potential measurement device 1 is placed on, for example, a mounting table (not illustrated) so that the measuring plane 1a faces vertically upward. A cell suspension L1 is dropped onto the measuring plane 1a. FIG. 3 is a cross-sectional view schematically illustrating the configuration example of the cell potential measurement device 1 in a state where the cell suspension L1 is dropped. The volume of the cell suspension L1 is, for example, about several μL (4 μL as a specific example). The cell suspension L1 is held on the measuring plane 1a. The cell suspension L1 contains cells of myocardium, nerve cells or the like, and these cells are to be deposited over time to form a sheet-like cell layer on the measuring plane 1a. The cell potential measurement device 1 measures the potential of the cell layer at each position on the measuring plane 1a. This allows monitoring the electrical activity of cells. Hereinafter, the configuration of the cell potential measurement device 1 will be described.

The cell potential measurement device 1 includes a plurality of working electrodes 10 and a reference electrode 20 provided on the measuring plane 1a. The plurality of working electrodes 10 are arranged two-dimensionally in a region R1 in plan view (that is, when viewed along the Z-axis direction). In other words, the plurality of working electrodes 10 are provided in the region R1 dispersedly in the X-axis direction and the Y-axis direction. Hereinafter, the region R1 is referred to as a working region RE In the example of FIG. 1, the plurality of working electrodes 10 are arranged in a matrix in the working region R1 of which X-axis direction and the Y-axis direction as rows and columns, respectively. Further, in the example of FIG. 1, although the working electrodes 10 of 4 rows by 4 columns is illustrated, the number of working electrodes 10 is not limited thereto and can be changed as appropriate. Such a plurality of working electrodes 10 may also be referred to as a multi-spot electrode array.

In the example of FIG. 1, each working electrode 10 has a rectangular shape in plan view, and one side thereof is arranged along the X-axis direction. One side of a virtual quadrangular region connecting the working electrodes 10 located at the four corners of the plurality of working electrodes 10 is set to, for example, several mm One side of each working electrode 10 is set to, for example, several hundred μm. For the material of the working electrodes 10, for example, at least one metal material of gold (Au), platinum (Pt) and titanium (Ti), or a conductive compound such as titanium nitride (TiN) or indium tin oxide (InSnO) is adoptable.

The reference electrode 20 is provided outside the working region R1 in plan view. In the example of FIG. 1, although four reference electrodes 20 are provided, the number thereof is not limited thereto and can be changed as appropriate. In the example of FIG. 1, each of the four reference electrodes 20 is provided at the apex of a virtual square whose side is along the X-axis direction. The center of the virtual square coincides with the center of the working region R1. For the material of the reference electrodes 20, for example, at least one metal material of gold (Au), platinum (Pt) and titanium (Ti), or a conductive compound such as titanium nitride (TiN) or indium tin oxide (InSnO) is adoptable as well.

And, in the example of FIG. 1, each reference electrode 20 has a rectangular shape in plan view, and one side thereof is arranged along the X-axis direction as well. The size of the reference electrode 20 in plan view may be set larger than that of the working electrode 10. For example, the size of the reference electrode 20 may be set to 5 times or more the size of the working electrode 10. Having the size of the reference electrode 20 increased in this manner, the impedance of the reference electrode 20 can be reduced. On the other hand, having the size of the working electrode 10 reduced, the working electrode 10 can measure the potential with high spatial resolution.

As illustrated in FIG. 1, the cell potential measurement device 1 also includes a plurality of wires 11 and wires 21. Each of the plurality of wires 11 is drawn from the respective plurality of working electrodes 10. The wires 11 extend from the working electrodes 10, respectively, toward the outside of the hydrophobic region R2 (described later) and are electrically connected to a processing device (for example, an arithmetic processing device) (not illustrated). As a result, the potentials of the working electrodes 10 are input to the processing device. In the example of FIG. 1, the plurality of wires 11 drawn from the respective plurality of working electrodes 10 extend along the X-axis direction, and extend further outward through between pairs of reference electrodes 20 arranged in the Y-axis direction. In the example of FIGS. 2 and 3, the wires 11 are omitted in order to avoid the complexity of the illustration. For the material of the wires 11, for example, at least one metal material of gold (Au), platinum (Pt) and titanium (Ti), or a conductive compound such as titanium nitride (TiN) or indium tin oxide (InSnO) is adoptable as well.

The wires 21 are drawn from the respective reference electrodes 20 and are electrically connected to the processing device (not illustrated). In the example of FIG. 1, the wires 21 each connected to two adjacent reference electrodes 20 in the X-axis direction includes two branch lines 211 and a common line 212. One end of each of the two branch lines 211 is connected to the reference electrode 20, and the other end is commonly connected to one end of the common line 212. The other end of the common line 212 is connected to the processing device. In the example of FIG. 1, the branch lines 211 extend in an arc shapes, and the common lines 212 extend on the side opposite to the working region R1. The wires 21 extend outside the hydrophobic region R2 described later. For the material of the wires 21, for example, at least one metal material of gold (Au), platinum (Pt) and titanium (Ti), or a conductive compound such as titanium nitride (TiN) or indium tin oxide (InSnO) is adoptable as well.

The cell potential measurement device 1 also includes an insulating film 30. The insulating film 30 covers the plurality of wires 11 and wires 21 and protects the wires 11 and the wires 21. The main surface on the +Z side of the insulating film 30 forms a part of the measuring plane 1a of the cell potential measurement device 1. As the material of the insulating film 30, for example, an insulating material such as silicon oxide or a resin (polyimide, acrylic, epoxy, etc.) can be adopted.

A plurality of openings 30b are formed in the insulating film 30 at positions opposite to at least parts of the main surfaces on the +Z side of the plurality of working electrodes 10. Therefore, the insulating film 30 does not cover at least the parts of the main surfaces of the working electrodes 10. In other words, at least parts of the main surfaces of the working electrodes 10 are exposed to the outside through the openings 30b, and form a part of the measuring plane 1a of the cell potential measurement device 1. The openings 30b of the insulating film 30 each have a rectangular shape in plan view, similarly to the working electrodes 10, for example. In the illustrated example, the insulating film 30 covers only the peripheral edge of the main surface of each working electrode 10.

The insulating film 30 is formed with an opening 30c at a position opposite to at least a part of the main surface on the +Z side of each reference electrode 20. Therefore, the insulating film 30 does not cover at least the parts of the main surfaces of the reference electrodes 20. In other words, at least parts of the main surfaces of the reference electrodes 20 are exposed to the outside through the openings 30c, and form a part of the measuring plane 1a of the cell potential measurement device 1. The openings 30c of the insulating film 30 each have a rectangular shape in plan view, similarly to the reference electrodes 20, for example. In the illustrated example, the insulating film 30 covers only the peripheral edge of the main surface of each reference electrode 20.

As illustrated in FIG. 2, the cell potential measurement device 1 also includes a substrate 40. The substrate 40 is, for example, a transparent glass substrate. The substrate 40 is provided such that the thickness direction thereof is along the Z-axis direction. The working electrodes 10, the reference electrodes 20, the wires 11 and the wires 21 are formed on the main surface on the +Z side of the substrate 40. The insulating film 30 is formed on this structure while avoiding covering the openings 30b and the openings 30c. The insulating film 30 covers the wires 11 and the wires 21 and protects the wires 11 and the wires 21 against external factors.

The operator drops the cell suspension L1 onto the measuring plane 1a of the cell potential measurement device 1. At this point, the operator drops the cell suspension L1 such that the cell suspension L1 covers the working region R1 and does not come into contact with any reference electrode 20. As a result, as illustrated in FIG. 3, no cell suspension L1 is present directly above the reference electrodes 20, whereas the cell suspension L1 is present directly above the working electrodes 10. The cells in the cell suspension L1 are deposited by their own weight to form a cell layer on the measuring plane 1a.

The processing device calculates a value obtained by subtracting the reference potential of the reference electrodes 20 (for example, the average value of the potentials of the four reference electrodes 20) from the potential of each working electrode 10 as a measurement potential at the position of each working electrode 10. By obtaining the measurement potential using the reference potential in this manner, external noise can be reduced. The changes in the measurement potential with time indicate the electrical activity in the cell layer.

In the cell potential measurement device 1, the contact angle in the region R2 (hereinafter, also referred to as hydrophobic region R2) between the reference electrodes 20 and the working region R1 of the measurement plane 1a is larger than the contact angle in the working region RE In other words, the wettability of the hydrophobic region R2 is lower than that of the working region RE The contact angle referred to here is a contact angle for a liquid (for example, cell suspension L1) on the measuring plane 1a. The contact angle in the working region R1 is a contact angle in a state where the contour of the contact surface between the liquid and the measuring plane 1a is located in the working region RE The contact angle in the hydrophobic region R2 is a contact angle in a state where the contour of the contact surface between the liquid and the measuring plane 1a is located in the hydrophobic region R2.

In the example of FIGS. 1 and 2, the insulating film 30 has a concavo-convex shape for hydrophobization in the hydrophobic region R2. The concavo-convex shape for hydrophobicity here referred to means a concavo-convex shape enough to make the contact angle larger than that in the case where the insulating film 30 is substantially flat. For example, a case where a hydrophobic material (for example, polyimide, acrylic, epoxy, etc.) is adopted as the material of the insulating film 30 will be described. The hydrophobic material referred to here is a material that makes the contact angle 90 degrees or more when a liquid (for example, pure water) is dropped on a substantially flat surface formed by the material. By forming, for example, a micron-order concavo-convex shape on the insulating film 30, the contact angle in the region where the concavo-convex shape is formed is made large.

As a more specific example, the insulating film 30 has a concavo-convex shape in the radial cross section about the center of the working region RE The pitch of the concave and convex in the hydrophobic region R2 of the insulating film 30 can be set to, for example, about several μm (3 μm as a specific example). The pitch of this concave and convex is smaller than, for example, the pitch of the working electrodes 10. Further, the width of the convex portions and the width of the concave portions in the hydrophobic region R2 of the insulating film 30 are also set to about several μm (3 μm as a specific example). The width of the concave portions in the hydrophobic region R2 of the insulating film 30 are narrower than, for example, the width of the openings 30b of the insulating film 30.

Meanwhile, a hydrophilic material (for example, silicon oxide) may also be adopted as the material of the insulating film 30. The hydrophilic material referred to here is a material that makes the contact angle less than 90 degrees when a liquid (for example, pure water) is dropped on a substantially flat surface formed by the material.

In this case, the pitch of the concavo-convex shape of the insulating film 30 in the hydrophobic region R2, the width of the concave portions, and the width of the convex portions are set so that entering of the cell suspension L1 into the inside of the concave portions of the insulating film 30 can be prevented. For example, the pitch, the width of the concave portions and the width of the convex portions, is set to, for example, less than 1 μm. Such a concavo-convex shape is referred to as the Cassie Baxter model. In the example of FIG. 3, no cell suspension L1 has entered the inside of the concave portions of the insulating film 30, but gas (for example, air) fills in the inside of the concave portions. In this case, even if a hydrophilic material is adopted as the material of the insulating film 30, the contact angle in the hydrophobic region R2 is made large due to the concavo-convex shape.

In the example of FIGS. 2 and 3, the depth of the concave portions in the hydrophobic region R2 of the insulating film 30 is equal to the thickness of the insulating film 30. Therefore, in the example of FIGS. 2 and 3, the main surface on the +Z side of the substrate 40 is exposed to the outside as the bottom surfaces of the concave portions of the insulating film 30, and forms a part of the measuring plane 1a of the cell potential measurement device 1. However, the main surface on the +Z side of the substrate 40 does not necessarily have to be exposed to the outside, and the depth of the concave portions may be less than the thickness of the insulating film 30.

In the example of FIG. 1, the insulating film 30 includes a plurality of grooves 30a in the hydrophobic region R2. In the example of FIG. 1, substantially arc-shaped grooves 30a are formed substantially concentrically. The center of the arc of each groove 30a substantially coincides with the center of the working region R1. The grooves 30a form the concave portions of the insulating film 30, and the portions interposed between the grooves 30a form the convex portions of the insulating film 30. As a result, the concavo-convex shape is formed on the insulating film 30.

In the example of FIG. 1, the concavo-convex shape of the insulating film 30 is not formed directly above the wires 11, and is formed in regions avoiding directly above the wires 11. As a specific example, each groove 30a has a substantial arc-shape obtained by separating a substantially circular shape in the circumferential direction with the regions where the wires 11 are present as separation regions. Conversely, the main surface on the +Z side of the insulating film 30 is substantially flat directly above the wires 11. Therefore, the film thickness of the insulating film 30 directly above the wires 11 is made substantially uniform. Thus, the wires 11 are protected substantially uniformly.

<Manufacturing Method>

Figure 4:
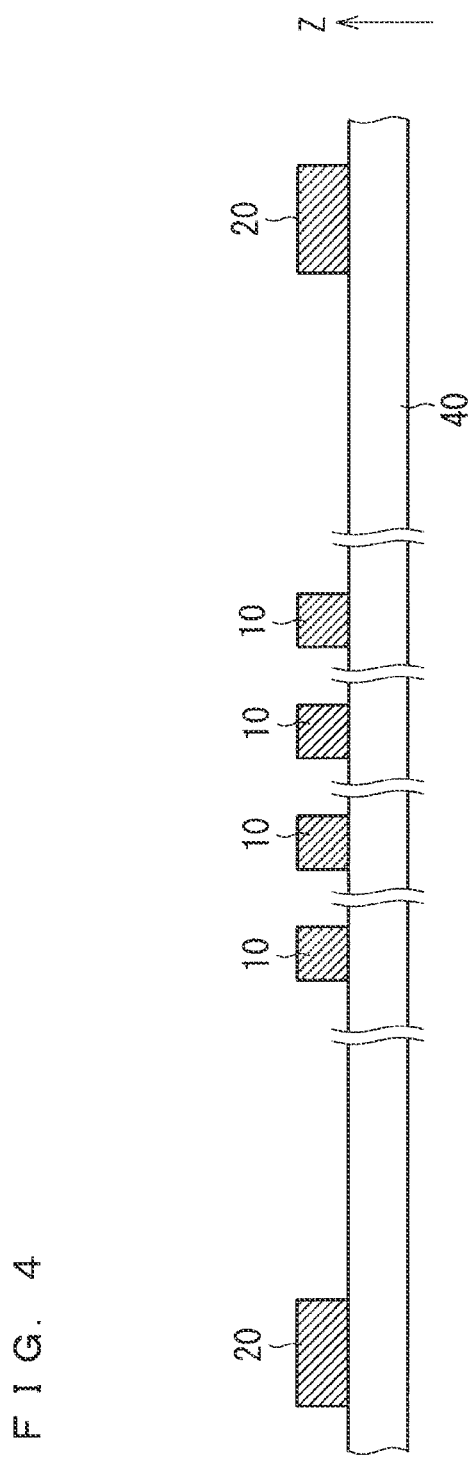
FIG. 4 A cross-sectional view schematically illustrating a configuration example in the process of manufacturing the cell potential measurement device.
Figure 5:
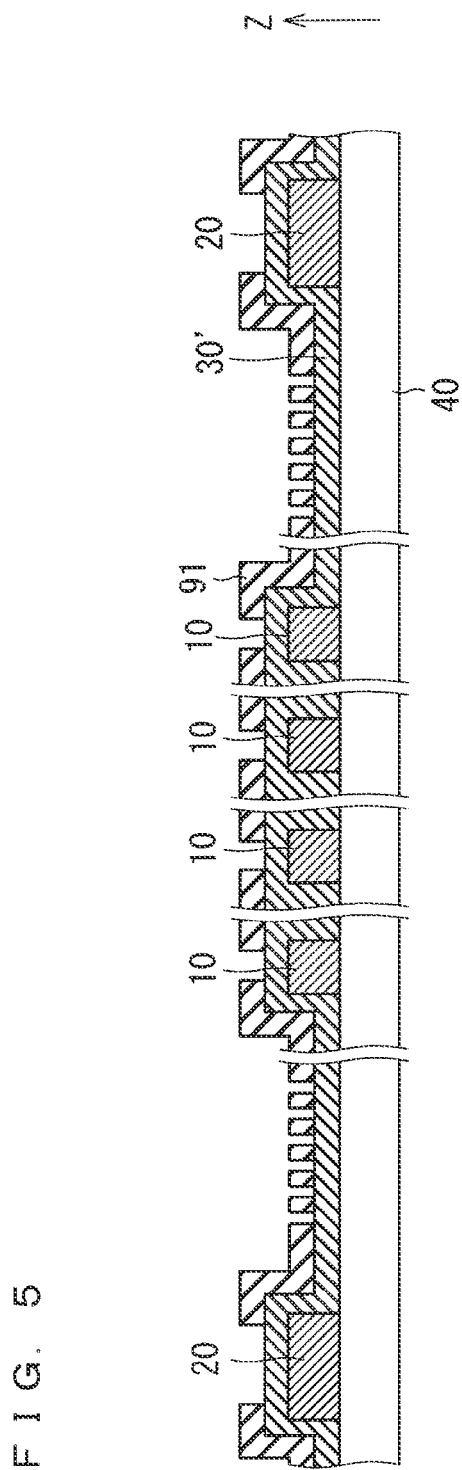
FIG. 5 A cross-sectional view schematically illustrating the configuration example in the process of manufacturing the cell potential measurement device.

Next, an example of a manufacturing method of the cell potential measurement device 1 will be described. FIGS. 4 and 5 are cross-sectional views schematically illustrating an example of a configuration in each step in the manufacturing method of the cell potential measurement device 1. FIGS. 4 and 5 illustrate the example of the configurations in the cross sections corresponding to the A-A cross section of FIG. 1, and the wires 11 are not illustrated.

The working electrodes 10, the reference electrodes 20, the wires 11 and the wires 21 are first formed on the main surface on the +Z side of the substrate 40. For example, first, a metal conductive film is formed on the main surface on the +Z side of the substrate 40 by a liquid phase film deposition method or a vapor phase film deposition method. The thickness of the conductive film is, for example, several tens of nm (80 nm as a specific example). Next, a resist is patterned on the main surface on the +Z side of the conductive film by a lithography method. The resist pattern has a shape corresponding to the working electrodes 10, the reference electrodes 20, the wires 11 and the wires 21. Next, the conductive film is etched using the resist as a mask to form the working electrodes 10, the reference electrodes 20, the wires 11, and the wires 21. Next, the resist is removed. Accordingly, the structure illustrated in FIG. 4 can be obtained. Noted that the working electrodes 10, the reference electrodes 20, the wires 11, and the wires 21 may also be formed by the lift-off technology.

Next, an insulating film 30' is formed on the main surface on the +Z side of the structure by, for example, the liquid phase film deposition method or the vapor phase film deposition method (see also FIG. 5). The thickness of the insulating film 30' is, for example, several hundreds of nm (340 nm as a specific example). Next, a resist 91 is patterned on the main surface on the +Z side of the insulating film 30' by the lithography method. The pattern of the resist 91 has a shape corresponding to the grooves 30a, the openings 30b, and the openings 30c of the insulating film 30. Next, the insulating film 30' is etched using the resist 91 as a mask to form the insulating film 30. At this point, the substrate 40 may be etched in the grooves 30a to form a concavo-convex shape on the main surface on the +Z side of the substrate 40. Next, the resist 91 is removed.

As described above, the cell potential measurement device 1 illustrated in FIGS. 1 and 2 is manufactured.

According to the cell potential measurement device 1, the insulating film 30 is formed with a concavo-convex shape for hydrophobization in the hydrophobic region R2. Accordingly, the contact angle in the hydrophobic region R2 is made large. In the cell potential measurement device 1, the contact angle in the hydrophobic region R2 is larger than the contact angle in the working region R1.

By the way, as the contact angle is larger, the cell suspension L1 is held in a raised state on the measuring plane 1a of the cell potential measurement device 1. In other words, the smaller the contact angle, the thinner the cell suspension L1 is held on the measuring plane 1a of the cell potential measurement device 1. Therefore, if the volumes of the cell suspension L1 are equal to each other, the smaller the contact angle of the measurement surface 1a, the more the cell suspension L1 spreads outward in plan view.

Figure 6:
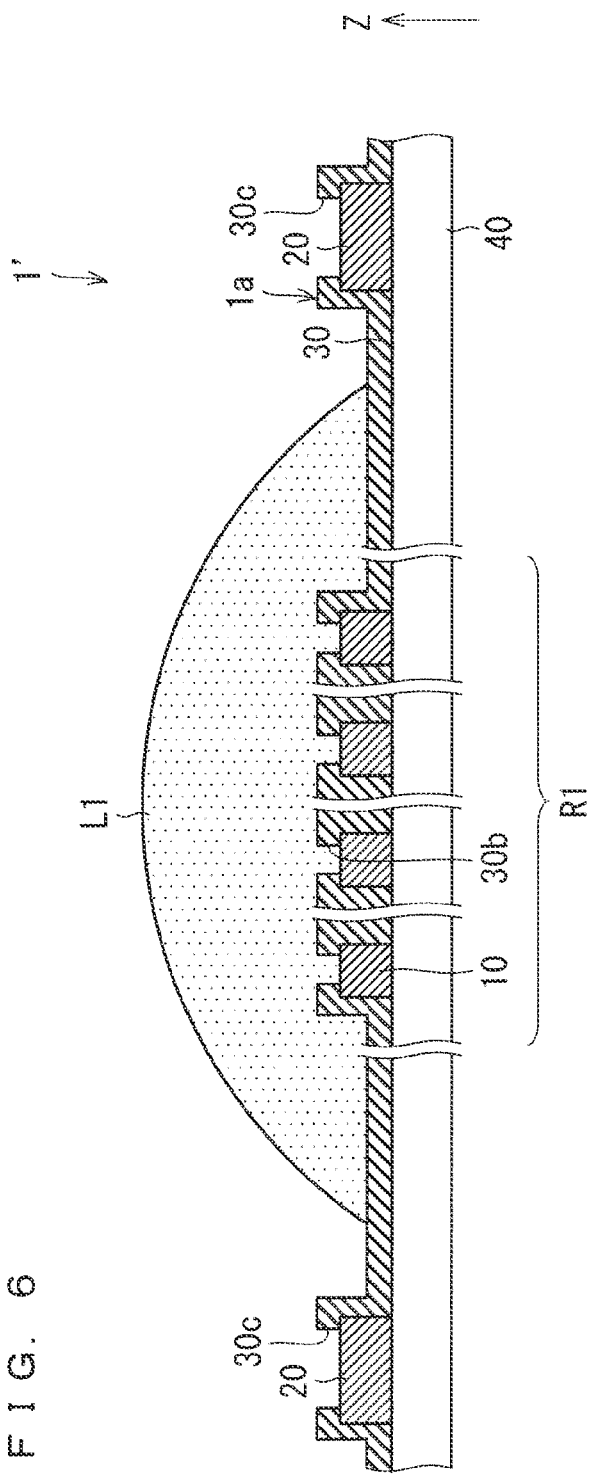
FIG. 6 A cross-sectional view schematically illustrating a configuration example of a cell potential measurement device according to a comparative example in a state where a cell suspension is dropped.

Here, a cell potential measurement device 1' in which the insulating film 30 is flat in the hydrophobic region R2 will also be considered. FIG. 6 is a cross-sectional view schematically illustrating a configuration example of the cell potential measurement device 1' in a state where the cell suspension L1 is dropped. In FIGS. 3 and 6, the volumes of cell suspension L1 are equal to each other, here, that is 4 μL.

As illustrated in FIGS. 3 and 6, the edge (contour) of the cell suspension L1 is located between the working region R1 and the reference electrodes 20. In the cell potential measurement device 1' of FIG. 6, the cell suspension L1 spreads in the horizontal direction. This is because the insulating film 30 is substantially flat in the region between the working region R1 and the reference electrodes 20, and the contact angle therein is small. The contact angle is, for example, 67 degrees.

When the cell suspension L1 spreads outward as described, the cells in the cell suspension L1 are deposited over a larger area. This reduces the density of the cell layer in plan view that deposited on the working region RE Remarkably, regions where few cell layers are formed can be localized in plan view. That is, in the measuring plane 1a of the cell potential measurement device 1', regions where the cell layer is dense and regions where the cell layer is sparse can be mixed. In this case, the measurement accuracy of the working electrodes 10 located directly below the sparse cell layer is low.

On the other hand, in the cell potential measurement device 1 of FIG. 3, the cell suspension L1 rises vertically upward, and the thickness thereof is larger than that of the cell suspension L1 of FIG. 6. This is because the insulating film 30 has a concavo-convex shape for hydrophobization in the hydrophobic region R2 between the working region R1 and the reference electrodes 20, and the contact angle therein is large. The contact angle is, for example, 120 degrees. Therefore, in the cell potential measurement device 1, the area of the cell suspension L1 in plan view is small.

Accordingly, the cells in the cell suspension L1 are deposited into a relatively small area of a region. Consequently, improvement in the density of the cell layer formed on the measuring plane 1a in plan view is ensured. Therefore, each working electrode 10 can more appropriately output the potential at each position of the cell layer to the processing device. In other words, the cell potential measurement device 1 can measure the potential at each position of the cell layer with high measurement accuracy.

Further, in the above example, the hydrophobic region R2 has a substantially annular band shape surrounding the working region RE The ratio of the concavo-convex shape (grooves 30a) to the hydrophobic region R2 in the circumferential direction is, for example, 50% or more, more preferably 70% or more. Further, in the example of FIG. 1, a concavo-convex shape (grooves 30a) is formed in at least a part of each of the four regions obtained by dividing the hydrophobic region R2 into four equal parts in the circumferential direction. According to this, the spread of the cell suspension L1 on the measuring plane 1a can be controlled in a more isotropic manner.

Further, according to the cell potential measurement device 1, the contact angle in the hydrophobic region R2 is large; therefore, the cell suspension L1 is less likely to spread to the reference electrodes 20. If the cell suspension L1 reaches the reference electrodes 20, a cell layer is also formed on the main surface on the +Z side of the reference electrodes 20. Therefore, potentials corresponding to the activity of cells in the cell layer are also applied to the reference electrodes 20. This deteriorates the measurement accuracy significantly. However, according to the cell potential measurement device 1, the potential spread of the cell suspension L1 to the reference electrodes 20 can be reduced, and such deterioration of measurement accuracy can be suppressed.

Figure 7:
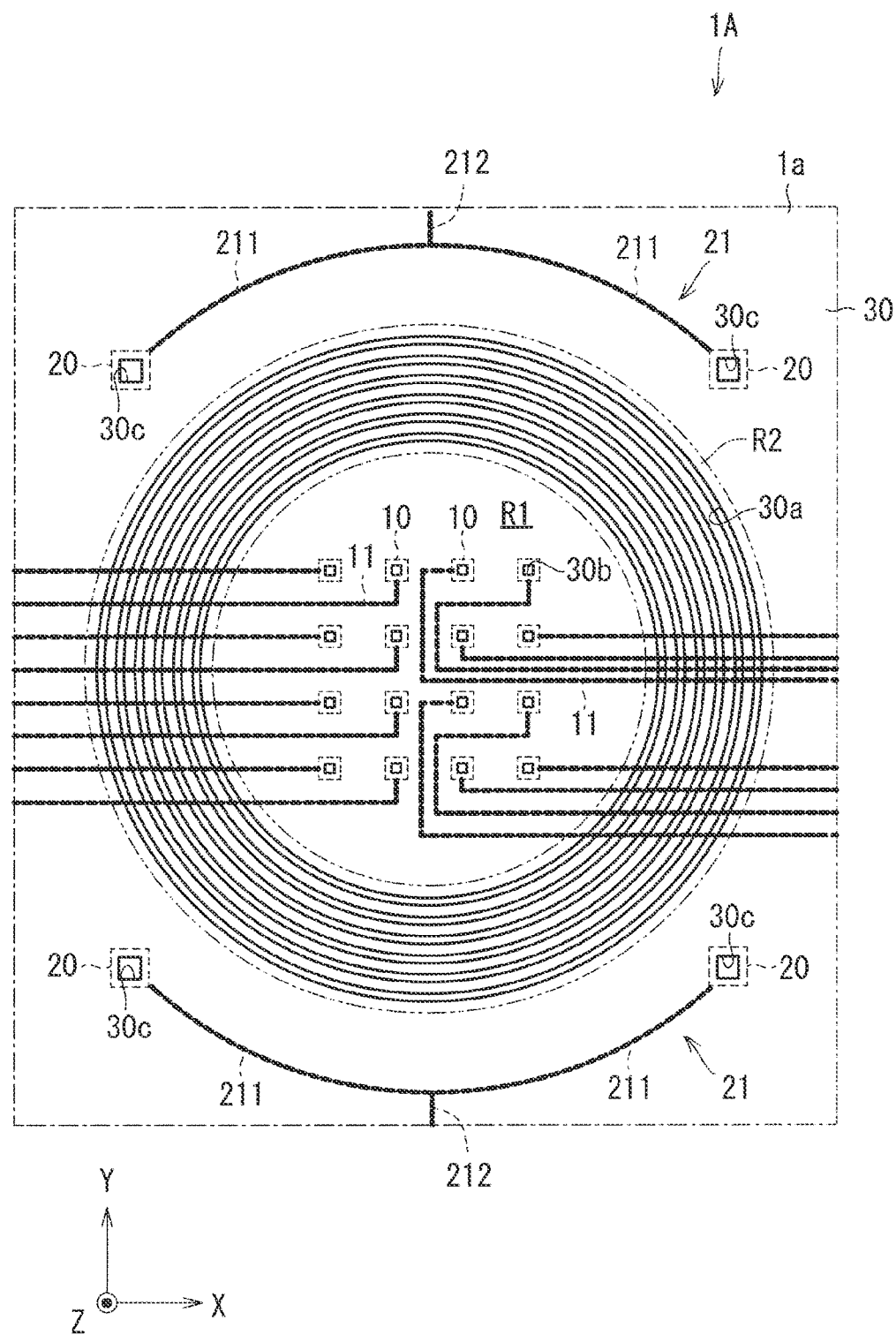
FIG. 7 A plan view schematically illustrating another configuration example of a cell potential measurement device.

In the above example, in the insulating film 30, the concavo-convex shape is formed in the regions avoiding directly above the wires 11. However, this is not the only case to be adopted. FIG. 7 is a plan view schematically illustrating a configuration example of a cell potential measurement device 1A. The cell potential measurement device 1A has the same configuration as the cell potential measurement device 1 except for the concavo-convex shape of the insulating film 30. In the example of FIG. 7, a plurality of substantially circular grooves 30a are formed substantially concentrically. That is, the plurality of grooves 30a are formed over the entire circumference of the working region R1. Such grooves 30a are also formed directly above the wires 11. Accordingly, the contact angle in the hydrophobic region R2 as a whole is made large.

However, the wires 11 are required to be covered by the insulating film 30; therefore, the depth of the grooves 30a formed in the insulating film 30 is less than the thickness of the insulating film 30. That is, the grooves 30a of the insulating film 30 are shallower than the openings 30b and the openings 30c of the insulating film 30. For example, when the thickness of the insulating film 30 is 340 nm, the depth of the openings 30b and the openings 30c of the insulating film 30 is set to 340 nm, and the depth of the grooves 30a of the insulating film 30 is set to a lower value smaller than the depth of the openings 30b and the openings 30c, which is, for example, 240 nm. In this case, the minimum value of the thickness of the insulating film 30 directly above the wires 11 is 100 nm.

In the cell potential measurement device 1A, forming the grooves 30a, the openings 30b, and the openings 30c by one-time etching is difficult to accomplish. This is because when the insulating film 30' is etched to the depths of the openings 30b and the openings 30c, the grooves 30a are also etched to the same depth. Therefore, the etching for the grooves 30a is required to be performed in a step separated from the step for the etching for the openings 30b and the openings 30c.

Whereas, in the cell potential measurement device 1 in which the grooves 30a are formed in regions avoiding directly above the wires 11, the grooves 30a, the openings 30b and the openings 30c can be formed by one-time etching (see FIG. 5). Therefore, the cell potential measurement device 1 is manufactured in fewer steps than the cell potential measurement device 1A. Accordingly, the manufacturing cost of the cell potential measurement device 1 is more reduced than that of the cell potential measurement device 1A.

In the above example, in the insulating film 30, substantially arc-shape or substantially circular grooves 30a are formed substantially concentrically to form the concavo-convex shape. However, this is not the only case to be adopted. For example, in the insulating film 30, dot-shaped (for example, substantially columnar or substantially prismatic) convex portions or dot-shaped concave portions may also be two-dimensionally arranged in the hydrophobic region R2. Alternatively, the insulating film 30 may also have convex portions or concave portions, in the hydrophobic region R2, extending radially with respect to the center of the working region R1. In other words, the insulating film 30 may have a concavo-convex shape in the circumferential cross section with respect to the center of the working region R1.

Embodiment 2

Figure 8:
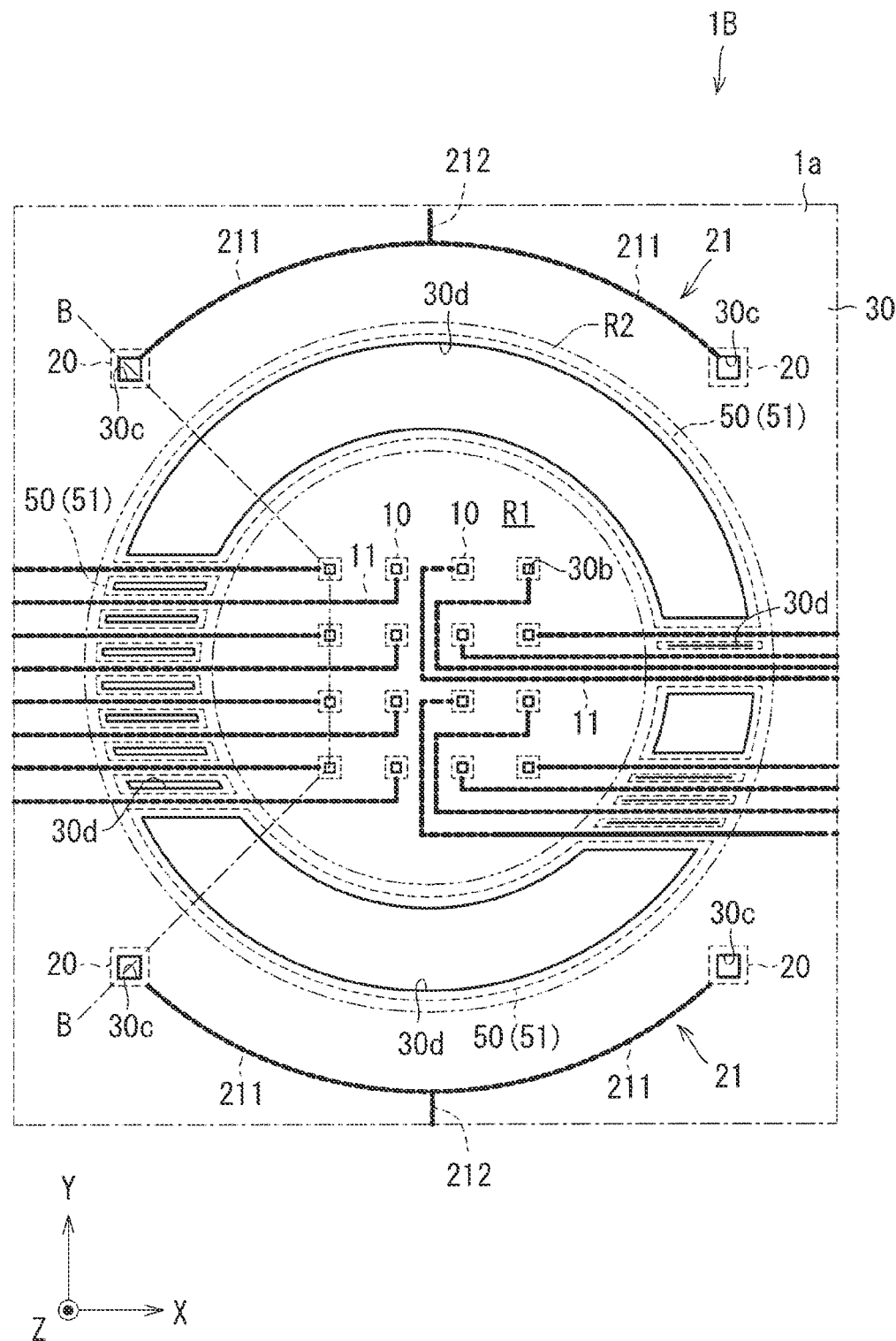
FIG. 8 A plan view schematically illustrating another configuration example of a cell potential measurement device.
Figure 9:
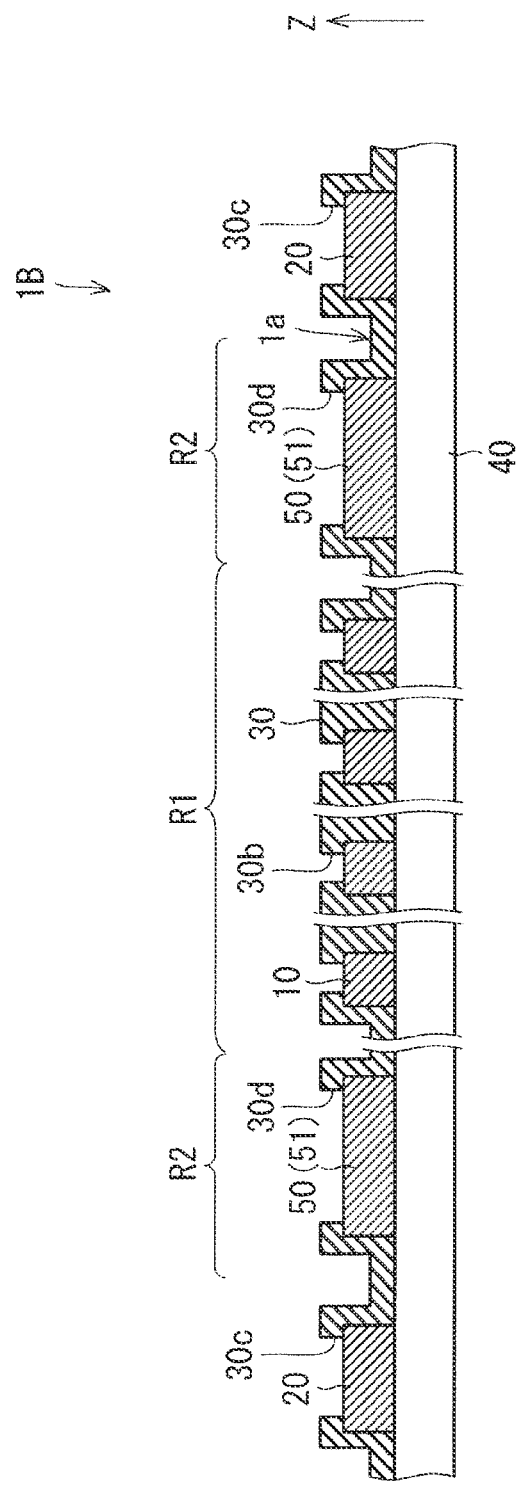
FIG. 9 A cross-sectional view schematically illustrating the other configuration example of the cell potential measurement device.

FIG. 8 is a plan view schematically illustrating a configuration example of a cell potential measurement device 1B, and FIG. 9 is a cross-sectional view schematically illustrating the configuration example of the cell potential measurement device 1B. FIG. 9 schematically illustrates the configuration example of in the B-B cross section of FIG. 8. Note that in FIG. 9, the wires 11 are not illustrated.

The cell potential measurement device 1B has the same configuration as the cell potential measurement device 1 except for a hydrophobic film and the shape of the insulating film 30. A hydrophobic film 50 is provided in the hydrophobic region R2, and at least a part of the main surface on the +Z side thereof forms a part of the measuring plane 1a. The contact angle in the hydrophobic film 50 is larger than the contact angle in the insulating film 30. In other words, the wettability of the hydrophobic film 50 is lower than that of the insulating film 30. As a specific example, the material of the hydrophobic film 50 is formed of, for example, at least one metal material of gold (Au), platinum (Pt) and titanium (Ti), or a conductive compound such as titanium nitride (TiN) or indium tin oxide (InSnO) (the hydrophobic film 50 may be subjected to a treatment for enlarging the contact angle by a manufacturing process described later or a surface treatment). Here, as the hydrophobic film 50, a metal film 51 being an example of a conductive film is adopted. The insulating film 30 is, for example, a silicon oxide film.

The metal film 51 is insulated from both the working electrodes 10 and the reference electrodes 20. In the example of FIG. 9, the metal film 51 is formed in the same layer as the working electrodes 10, the reference electrodes 20, the wires 11, and the wires 21. Therefore, the metal film 51 is formed apart from these elements in the XY plane. As illustrated in FIG. 8, the wires 11 cross the hydrophobic region R2 from the inside to the outside of the hydrophobic region R2; therefore, the metal film 51 is separated from the wires 11 in the circumferential direction in the hydrophobic region R2. As a specific example, the metal film 51 in plan view has a shape obtained by separating a substantially annular band shape in the circumferential direction with the regions where the wires 11 are present as separation regions. The working electrodes 10, the reference electrodes 20, and the wires 21 are provided in regions other than the hydrophobic region R2; therefore, the metal film 51 is also formed apart from these elements in the XY plane. In the example of FIG. 9, the main surface on the +Z side of the metal film 51 is substantially flat.

The insulating film 30 is formed with openings 30d at regions opposite to at least parts of the main surface on the +Z side of the metal film 51. Therefore, the insulating film 30 does not cover at least the parts of the main surfaces of the metal film 51. Therefore, at least parts of the main surfaces of the metal film 51 are exposed to the outside through the openings 30d, and form parts of the measuring plane 1a. In the example of FIG. 9, the insulating film 30 covers only the peripheral edges of the main surfaces of the metal film 50.

As the material of the metal film 51, for example, the same material as at least one of the working electrodes 10, the reference electrodes 20, the wires 11 and the wires 21 may be adopted. Here, as an example, the working electrodes 10, the reference electrodes 20, the wires 11, the wires 21, and the metal film 51 are made of the same material.

<Manufacturing Method>

Figure 10:
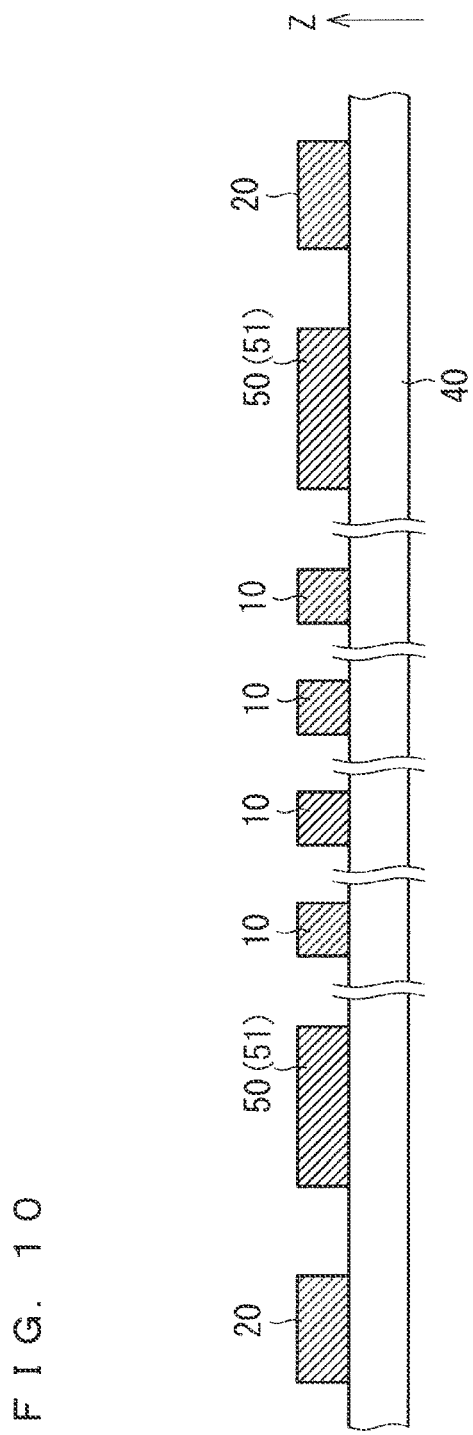
FIG. 10 A cross-sectional view schematically illustrating the other configuration example in the process of manufacturing the cell potential measurement device.
Figure 11:
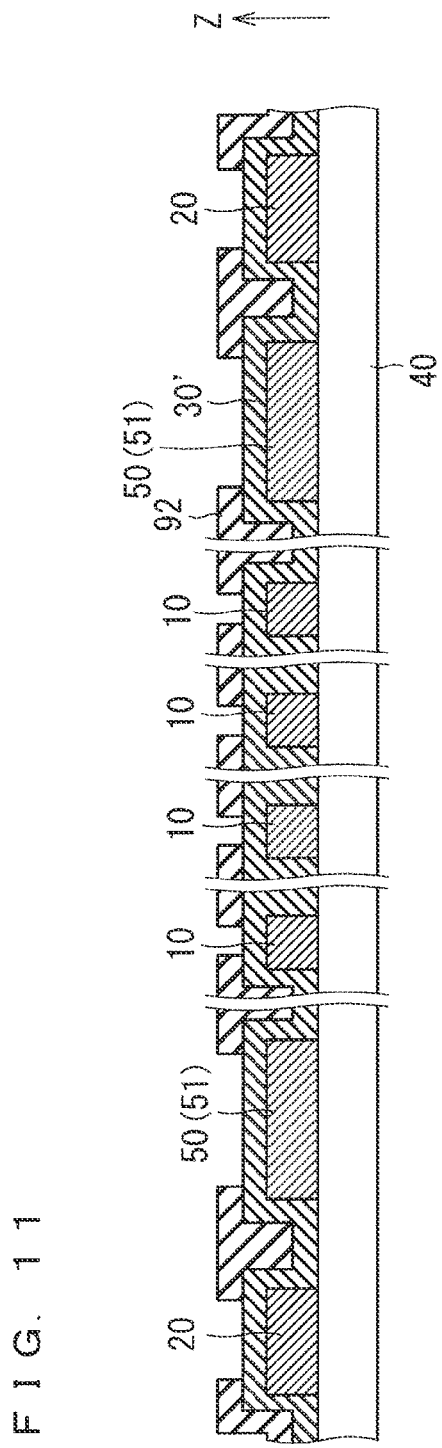
FIG. 11 A cross-sectional view schematically illustrating the other configuration example in the process of manufacturing the cell potential measurement device.

Next, an example of a manufacturing method of the cell potential measurement device 1B will be described. FIGS. 10 and 11 are cross-sectional views schematically illustrating an example of a configuration in each step in the manufacturing method of the cell potential measurement device 1B. FIGS. 10 and 11 illustrate the example of the configurations in the cross sections corresponding to the B-B cross section of FIG. 8, and the wires 11 are not illustrated.

The working electrodes 10, the reference electrodes 20, the wires 11, the wires 21, and the metal film 51 are first formed on the main surface on the +Z side of the substrate 40. For example, first, a metal conductive film is formed on the main surface on the +Z side of the substrate 40 by the liquid phase film deposition method or the vapor phase film deposition method. Next, a resist is patterned on the main surface on the +Z side of the conductive film by a lithography method. The resist pattern has a shape corresponding to the working electrodes 10, the reference electrodes 20, the wires 11, the wires 21, and the metal film 51. Next, the conductive film is etched using the resist as a mask to form the working electrodes 10, the reference electrodes 20, the wires 11, the wires 21, and the metal film 51. Next, the resist is removed. Accordingly, the structure illustrated in FIG. 10 can be obtained.

Next, an insulating film 30' is formed on the main surface on the +Z side of the structure by, for example, the liquid phase film deposition method or the vapor phase film deposition method (see also FIG. 11). Next, a resist 92 is patterned on the main surface on the +Z side of the insulating film 30' by the lithography method. The pattern of the resist 92 has a shape corresponding to the grooves 30a, the openings 30b, the openings 30c, and the openings 30d of the insulating film 30. Next, the insulating film 30' is etched using the resist 92 as a mask to form the insulating film 30. Next, the resist 92 is removed.

As described above, the cell potential measurement device 1B illustrated in FIGS. 8 and 9 is manufactured.

In the cell potential measurement device 1B, the contact angle in the hydrophobic region R2 is larger than the contact angle in the working region RE Therefore, in the cell potential measurement device 1B, the area of the cell suspension L1 dropped on the measuring plane 1a in plan view is small. Consequently, the cell layer is formed on the measuring plane 1a is made in higher density.

The ratio of the hydrophobic film 50 to the hydrophobic region R2 in the circumferential direction is, for example, 50% or more, more preferably 70% or more. Further, in the example of FIG. 8, the hydrophobic film 50 is formed in at least a part of each of the four regions obtained by dividing the hydrophobic region R2 into four equal parts in the circumferential direction. According to this, the spread of the cell suspension L1 on the measuring plane 1a can be controlled in a more isotropic manner.

In the example described above, the metal film 51 is formed in the same layer as the working electrodes 10, the reference electrodes 20, the wires 11, and the wires 21 and formed of the same material as that of these elements. Therefore, the metal film 51 can be formed at the same time as the time those elements are formed (see FIG. 10). Therefore, the manufacturing cost can be reduced.

Further, the contact angle is large on the hydrophobic film 50 (here, the metal film 51) in the hydrophobic region R2; therefore, the material of the insulating film 30 can be selected regardless of the contact angle in the hydrophobic region R2. For example, a hydrophilic material can be used as the material of the insulating film 30. It goes without saying that, in Embodiment 1, while a hydrophilic material can be used as the insulating film 30 by forming a fine concavo-convex shape (so-called Cassie Baxter model) on the insulating film 30, such a fine concavo-convex shape is not required to be formed in Embodiment 2.

Figure 12:
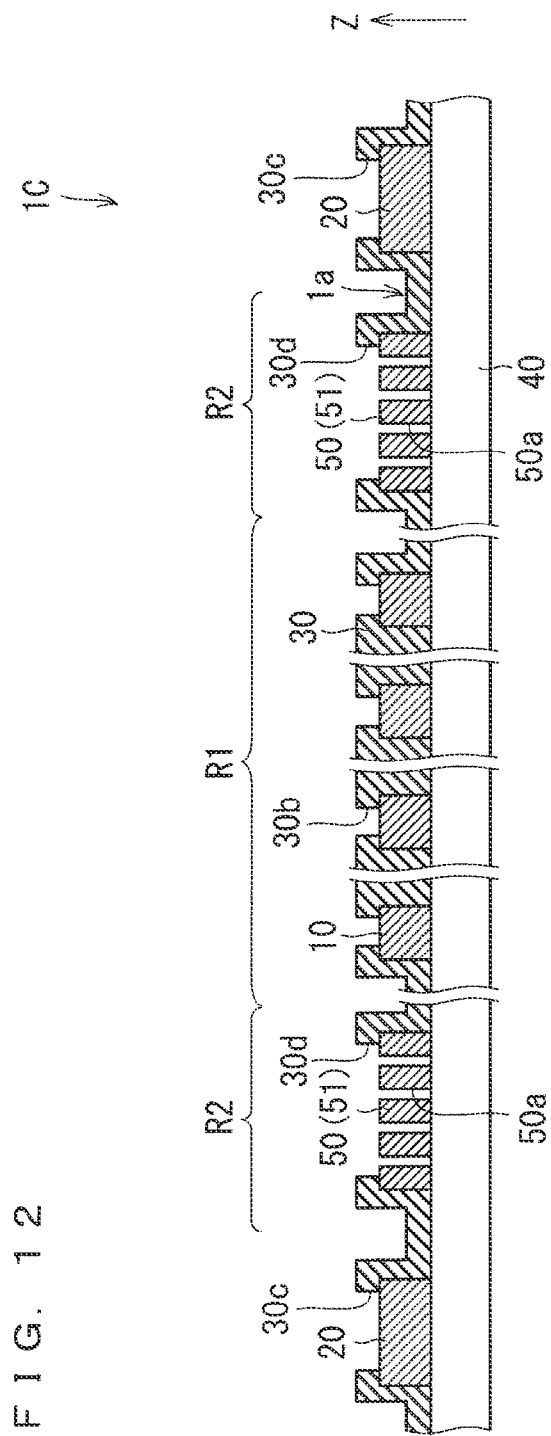
FIG. 12 A cross-sectional view schematically illustrating another configuration example of the cell potential measurement device.

On the other hand, in order to enlarge the contact angle further in the hydrophobic region R2, a concavo-convex shape for hydrophobization may be formed on the hydrophobic film 50 (for example, the metal film 51). FIG. 12 is a plan view schematically illustrating a configuration example of a cell potential measurement device 1C. The cell potential measurement device 1C has the same configuration as the cell potential measurement device 1B except for the shape of the hydrophobic film 50 (for example, the metal film 51).

In the cell potential measurement device 1C, the hydrophobic film 50 has, for example, a micron-order concavo-convex shape. Here, a case where a metal film 51 is adopted as the hydrophobic film 50 will be described. The metal film 51 has the concavo-convex shape, for example, in a radial cross section about the center of the working region R1. In the example of FIG. 12, a plurality of grooves 50a are formed in the metal film 51. The plurality of grooves 50a are formed in substantially arc-shape in substantially concentrically, as in the grooves 30a of Embodiment 1, for example. The grooves 50a may extend from one end to the other of the metal film 51 in the circumferential direction. The grooves 50a form concave portions, and the portions interposed between the grooves 50a form convex portions. As a result, the concave-convex shape is formed on the metal film 51.

The pitch of this concave and convex is smaller than, for example, the pitch of the working electrodes 10 and is set to, for example, about several μm. Further, the width of the convex portions and the width of the concave portions (the grooves 50a) of the metal film 51 are narrower than, for example, the width of the openings 30b directly above the working electrodes 10 of the insulating film 30, and are set to, for example, about several μm.

In the example of FIG. 12, the main surface on the +Z side of the substrate 40 is exposed to the outside at the bottom surfaces of the grooves 50a, and forms parts of the measuring plane 1a. However, the main surface of the substrate 40 does not necessarily have to be exposed to the outside, and the depth of the grooves 50a may be less than the thickness of the metal film 51.

Such a metal film 51 is formed, for example, as follows. First, a metal conductive film is formed on the +Z side main surface of the substrate 40. Next, a resist is patterned on the +Z side main surface of the conductive film by the lithography method. The resist pattern has a shape corresponding to the working electrodes 10, the reference electrodes 20, the wires 11, the wires 21, and the metal film 51. Next, the conductive film is etched using the resist as a mask. Consequently, the working electrodes 10, the reference electrodes 20, the wires 11 the wires 21, and the metal film 51 are formed on the main surface on the +Z side of the substrate 40.

In such a cell potential measurement device 1C, a concavo-convex shape for hydrophobization is formed on the metal film 51. Due to the concavo-convex shape, the contact angle in the hydrophobic region R2 is made even large. Accordingly, the area of the cell suspension L1 held on the measuring plane 1a in plan view can be reduced. Conversely, even if the volume of the cell suspension L1 dropped on the measuring 1a of the cell potential measurement device 1C is made large, the area of the cell suspension L1 in plan view does not greatly increase. Consequently, improvement in the density of the cell layer formed on the measuring plane 1a in plan view is ensured.

In the above example, in the metal film 51, substantially arc-shape grooves 50a are formed substantially concentrically to form the concavo-convex shape; however, this is not the only case to be adopted. For example, the metal film 51 may have dot-shaped convex portions or dot-shaped concave portions two-dimensionally arranged thereon. Alternatively, the metal film 51 may also have convex portions or concave portions extending radially with respect to the center of the working region RE In other words, the metal film 51 may have a concavo-convex shape in the circumferential cross section with respect to the center of the working region R1.

Further, in the cell potential measurement device 1C, the contact angle in the hydrophobic region R2 is made large due to the concavo-convex shape of the conductive film (for example, the metal film 51). Therefore, as the material of the conductive film, a material on which a contact angle formed thereon is made smaller than the contact angle formed on the material of the insulating film 30 may be adopted. That is, even if the contact angle of the conductive film when the main surface on the +Z side of the conductive film is flat is smaller than the contact angle of the insulating film 30 when the main surface on the +Z side of the insulating film 30 is flat, the contact angle of the conductive film need only be larger than the contact angle of the insulating film 30 by forming the concavo-convex shape for hydrophobization on the conductive film.

Figure 13:
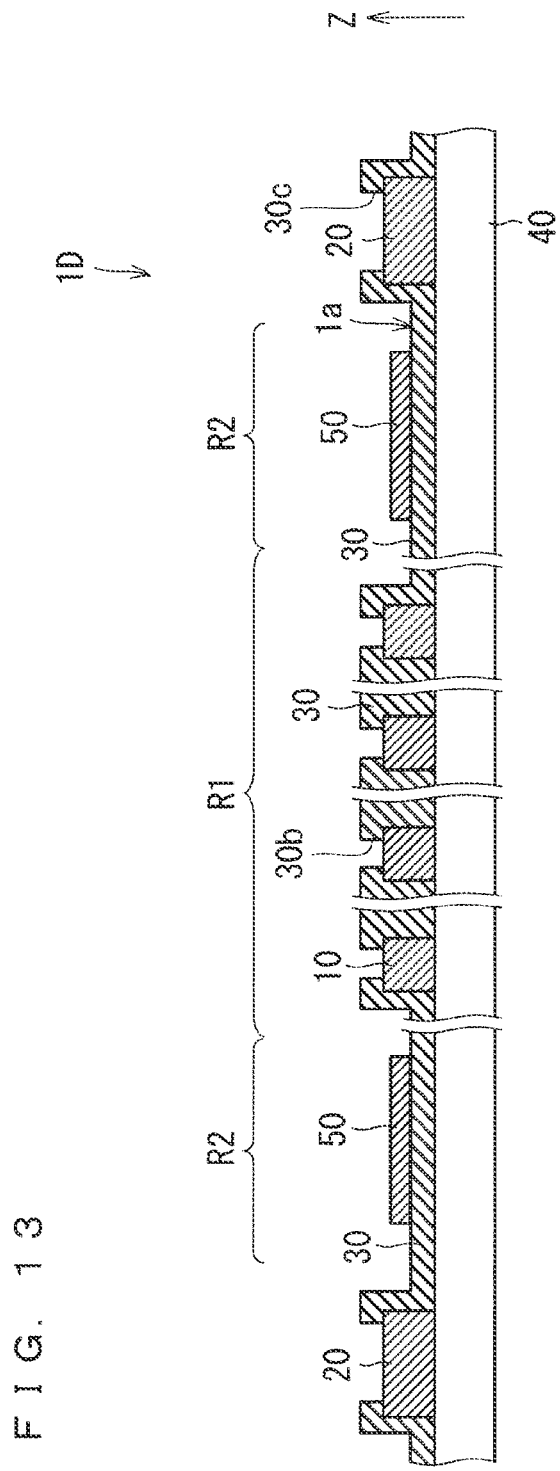
FIG. 13 A cross-sectional view schematically illustrating another configuration example of a cell potential measurement device.

In the example described above, the hydrophobic film 50 is formed in the same layer as the working electrodes 10, the reference electrodes 20, the wires 11, and the wires 21. However, this is not the only case to be adopted. At least a part of the +Z side main surface of the hydrophobic film 50 need only form a part of the measurement surface 1a, and for example, the hydrophobic film 50 may also be formed on the +Z side main surface of the insulating film 30. FIG. 13 is a cross-sectional view schematically illustrating a configuration example of a cell potential measurement device 1D. The cell potential measurement device 1D has the same configuration as the cell potential measurement device 1B except for a position of the hydrophobic film 50 and the shape of the insulating film 30.

In the example of FIG. 13, the insulating film 30 is present in the entire region of the hydrophobic region R2, and the main surface on the +Z side thereof is substantially flat in the hydrophobic region R2. Although not illustrated in FIG. 13, the insulating film 30 covers the wires 11; therefore, steps formed by the wires 11 can be formed on the main surface on the +Z side of the insulating film 30.

In the example of FIG. 13, the hydrophobic film 50 is formed in the hydrophobic region R2 on the main surface on the +Z side of the insulating film 30. In plan view, the hydrophobic film 50 has, for example, a substantially annular band shape surrounding the working region R1. The center of the annular shape of the hydrophobic film 50 substantially coincides with the center of the working region R1. In the example of FIG. 13, the main surface on the +Z side of the hydrophobic film 50 is substantially flat. However, if the steps formed by the wires 11 are formed on the main surface on the +Z side of the insulating film 30, steps formed by the steps can also be formed on the main surface on the +Z side of the hydrophobic film 50.

Such a hydrophobic film 50 is formed, for example, in a process through which a conductive film is formed on the main surface on the +Z side of the insulating film 30, and a resist is patterned on the main surface on the +Z side of the conductive film by a lithography method, and forming etching the conductive film using the resist as a mask.

In the cell potential measurement device 1D, the contact angle in the hydrophobic region R2 is larger than the contact angle in the working region RE Accordingly, the area of the cell suspension L1 held on the measuring plane 1a in plan view can also be reduced as in Embodiment 1.

In the above cell potential measurement device 1D, the main surface on the +Z side of the hydrophobic film 50 is substantially flat. However, the hydrophobic film 50 may have a concavo-convex shape for hydrophobization similar to that of the cell potential measurement device 1C. Due to the concavo-convex shape, the contact angle in the hydrophobic region R2 is made even larger.

In the above-mentioned cell potential measurement devices 1B to 1D, the hydrophobic film 50 need only be formed of a hydrophobic material having a lower wettability than that of the material of the insulating film 30, and is not necessarily formed of a metal. For example, a fluorine-based resin may also be used as the material for the hydrophobic film 50. Although the method for forming the hydrophobic film 50 is not particularly limited, the hydrophobic film 50 is formed as follows, for example. For example, the hydrophobic film 50 can be formed by applying a coating liquid containing a fluorine-based resin into the hydrophobic region R2 and drying the coating film.

Alternatively, oil or vaseline may be used as the material for the hydrophobic film 50. Although the method for forming the hydrophobic film 50 is not particularly limited, for example, the hydrophobic film 50 can be formed by applying oil or vaseline to the hydrophobic region R2 with a brush.

Embodiment 3

Figure 14:
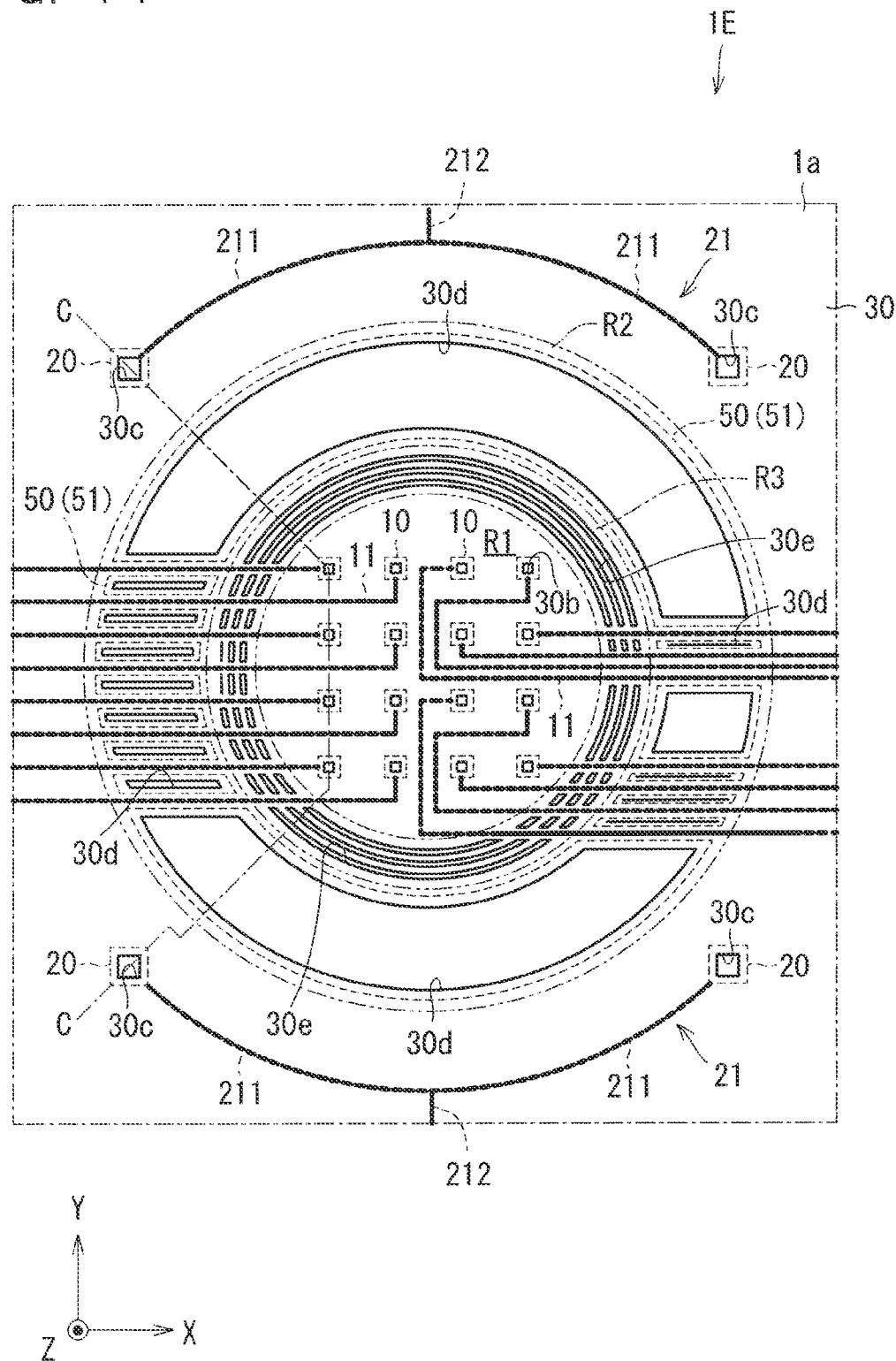
FIG. 14 A plan view schematically illustrating another configuration example of a cell potential measurement device.
Figure 15:
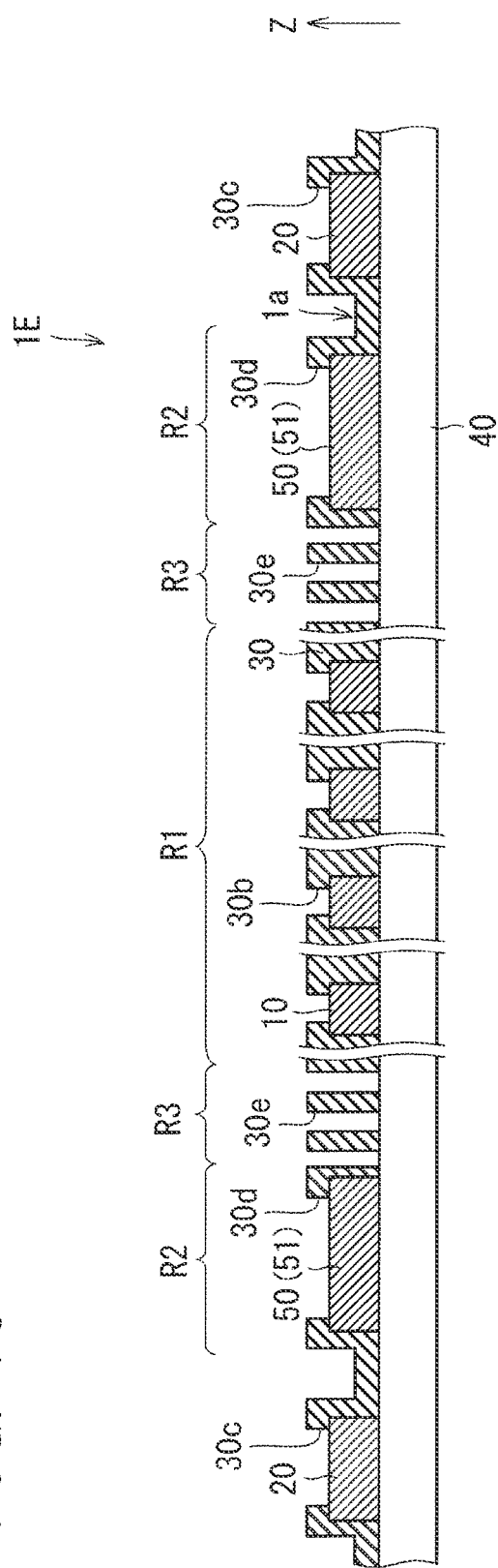
FIG. 15 A cross-sectional view schematically illustrating the other configuration example of the cell potential measurement device.

FIG. 14 is plan view schematically illustrating a configuration example of a cell potential measurement device 1E, and FIG. 15 is a cross-sectional view schematically illustrating the configuration example of the cell potential measurement device 1E. FIG. 15 schematically illustrates the configuration example of in the C-C cross section of FIG. 14. Note that in FIG. 15, the wires 11 are not illustrated.

The cell potential measurement device 1E has the same configuration as the cell potential measurement device 1B except for the presence of a hydrophilic region R3. The hydrophilic region R3 is a region present in the measuring plane 1a of the cell potential measurement device 1E between the working region R1 on which the working electrodes 10 are provided and the hydrophobic region R2. Further, in the example of FIG. 14, the hydrophilic region R3 has a substantially annular band shape surrounding the working region RE The contact angle in the hydrophilic region R3 is smaller than the contact angle in the working region RE In other words, the wettability of the hydrophilic region R3 is higher than that of the working region RE The contact angle in the hydrophilic region R3 here is a contact angle in a state where the contour of the contact surface between the liquid (for example, cell suspension L1) and the measuring plane 1a is located in the hydrophilic region R3.

Here, a hydrophilic material (for example, silicon oxide) is adopted as the material of the insulating film 30. In the example of FIGS. 14 and 15, the insulating film 30 has a concavo-convex shape for hydrophilicity in the hydrophilic region R3. The concave-convex shape for hydrophilicity here referred to means a concavo-convex shape enough to make the contact angle smaller than that in the case where the insulating film 30 is substantially flat. By forming a micron-order concavo-convex shape on the insulating film 30 formed by a hydrophilic material, for example, the contact angle in the region where the concavo-convex shape is made smaller.

In the example of FIG. 14, a plurality of grooves 30e are formed in the insulating film 30 as in the grooves 30a of Embodiment 1. In the example of FIG. 14, the plurality of substantially arc-shape grooves 30e are formed substantially concentrically in the insulating film 30. The grooves 30e form the concave portions of the insulating film 30, and the portions interposed between the grooves 30a form the convex portions of the insulating film 30. As a result, the concave-convex shape is formed on the insulating film 30.

The concavo-concave pitch and the width of the convex portions and the width of the concave portions in the hydrophilic region R3 of the insulating film 30 are set in the same manner as in the grooves 30a of Embodiment 1, for example. However, the pitch and size of the concavo-convex shape of the insulating film 30 are set to a degree that the cell suspension L1 can enter the concave portions (grooves 30e) of the insulating film 30. Such a concavo-convex shape is referred to as a Wenzel model. The pitch of the concave and convex in the hydrophilic region R3 of the insulating film 30 can be set to, for example, about several μm (3 μm as a specific example).

In the example of FIG. 14, the grooves 30e are not formed directly above the wires 11, and are formed in regions avoiding directly above the wires 11. Conversely, the insulating film 30 is substantially flat directly above the wires 11. Therefore, the film thickness of the insulating film 30 directly above the wires 11 is made substantially uniform and the wires 11 are protected uniformly.

In the example of FIG. 15, the main surface on the +Z side of the substrate 40 is exposed to the outside at the bottom surfaces of the grooves 30e, and forms parts of the measuring plane 1a. However, the main surface of the substrate 40 on the +Z side does not necessarily have to be exposed to the outside, and the depth of the grooves 30e may be less than the thickness of the insulating film 30.

As described above, the insulating film 30 has the concavo-convex shape for hydrophilicity in the hydrophilic region R3. Due to the concavo-convex shape, the contact angle in the hydrophilic region R3 is made smaller. That is, the wettability of the hydrophilic region R3 can be enhanced.

Such a cell potential measurement device 1E is manufactured, for example, as follows. For example, first, a metal conductive film is formed on the main surface of the substrate 40 on the +Z side by the liquid phase film deposition method or the vapor phase film deposition method. Next, a resist is patterned on the main surface on the +Z side of the conductive film by the lithography method. The resist pattern has a shape corresponding to the working electrodes 10, the reference electrodes 20, the wires 11, the wires 21, and a metal film 51. Next, the conductive film is etched using the resist as a mask to form the working electrodes 10, the reference electrodes 20, the wires 11, the wires 21, and the metal film 51. Next, the resist is removed.

Next, an insulating film is formed on the main surface of the substrate 40 on the +Z side of the structure by the liquid phase film deposition method or the vapor phase film deposition method. Next, a resist is patterned on the main surface on the +Z side of the insulating film by the lithography method. The resist pattern has a shape corresponding to the openings 30b, the openings 30c, the openings 30d and the grooves 30e of the insulating film 30. Next, the insulating film is etched using the resist as a mask to form the insulating film 30. In the example of FIG. 15, although the grooves 30e of the insulating film 30 is deeper than the openings 30b, the openings 30c and the openings 30d of the insulating film 30, the grooves 30e, the openings 30b, the openings 30c and the openings 30d of the insulating film 30 can be formed by performing etching one-time, because etching of the working electrodes 10 and the reference electrodes 20 are almost not etched. Next, the resist is removed.

As described above, the cell potential measurement device 1E illustrated in FIGS. 14 and 15 is manufactured. As described in detail below, according to the cell potential measurement device 1E, even if the droplet position of the cell suspension L1 deviates from the center of the working region R1, the cell suspension L1 is prone to covering the working region R1.

First, for comparison, the description of the cell potential measurement device 1B will be made (FIG. 8). In the working region R1 of the cell potential measurement device 1B, at least a part of the main surface on the +Z side of each working electrode 10 is exposed through the opening 30b. Here, the working electrodes 10 are formed of a hydrophobic material such as gold (Au). Therefore, the cell suspension L1 may not be less likely to spread in the horizontal direction in the working region R1.

Figure 16:
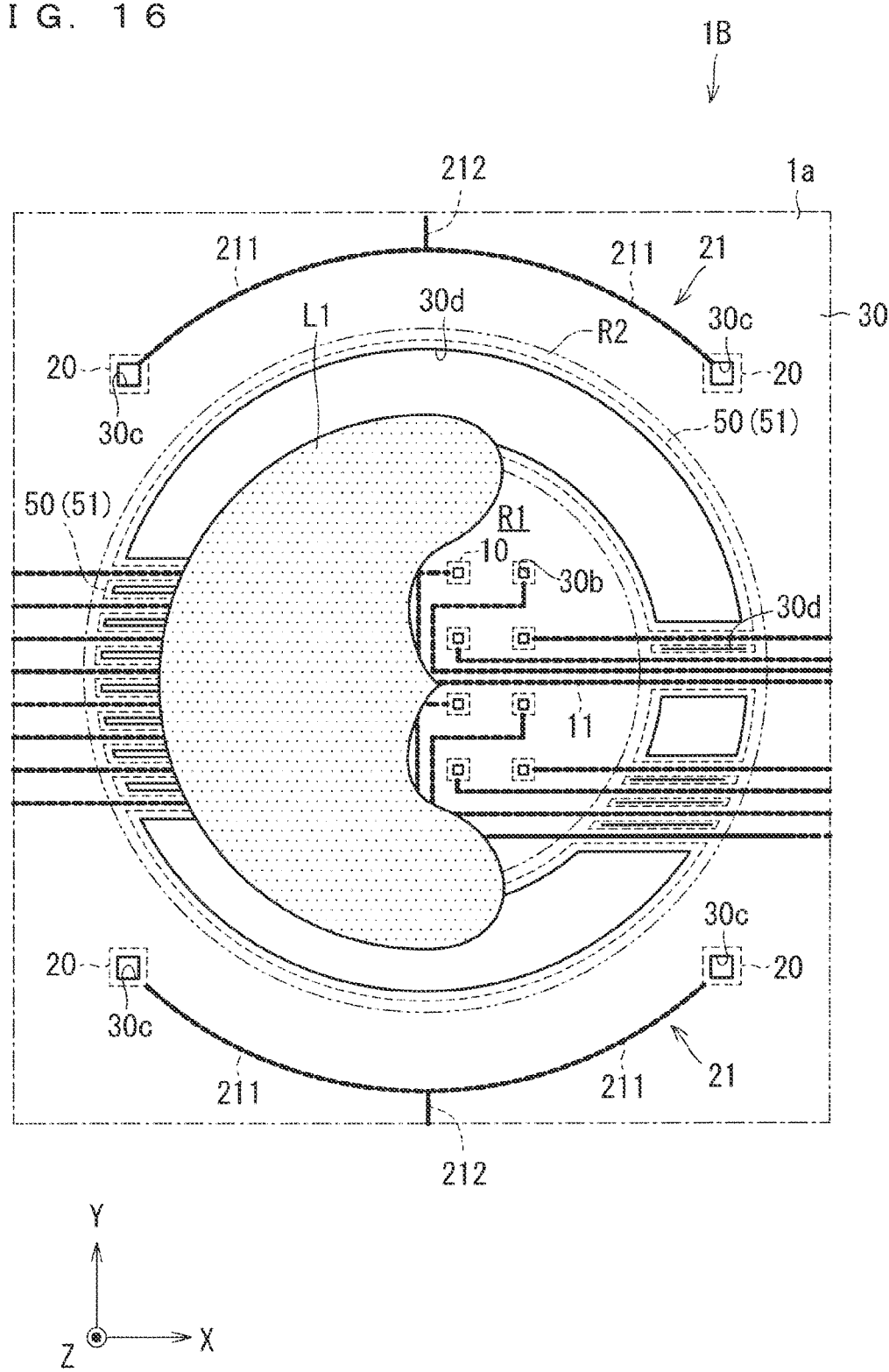
FIG. 16 A cross-sectional view schematically illustrating the other configuration example of the cell potential measurement device in a state where a cell suspension is dropped.

FIG. 16 is a plane view schematically illustrating a configuration example of the cell potential measurement device 1B in a state where the cell suspension L1 is dropped. In FIG. 16, the cell suspension L1 is illustrated in hatched pattern of sand. In the example of FIG. 16, the droplet position of the cell suspension L1 deviates from the center of the working region R1 to the −X side, and because of this, the cell suspension L1 does not spread over the entire working region R1 and a portion of the region on the +X side of the working region R1 is not covered by the droplet.

Figure 17:
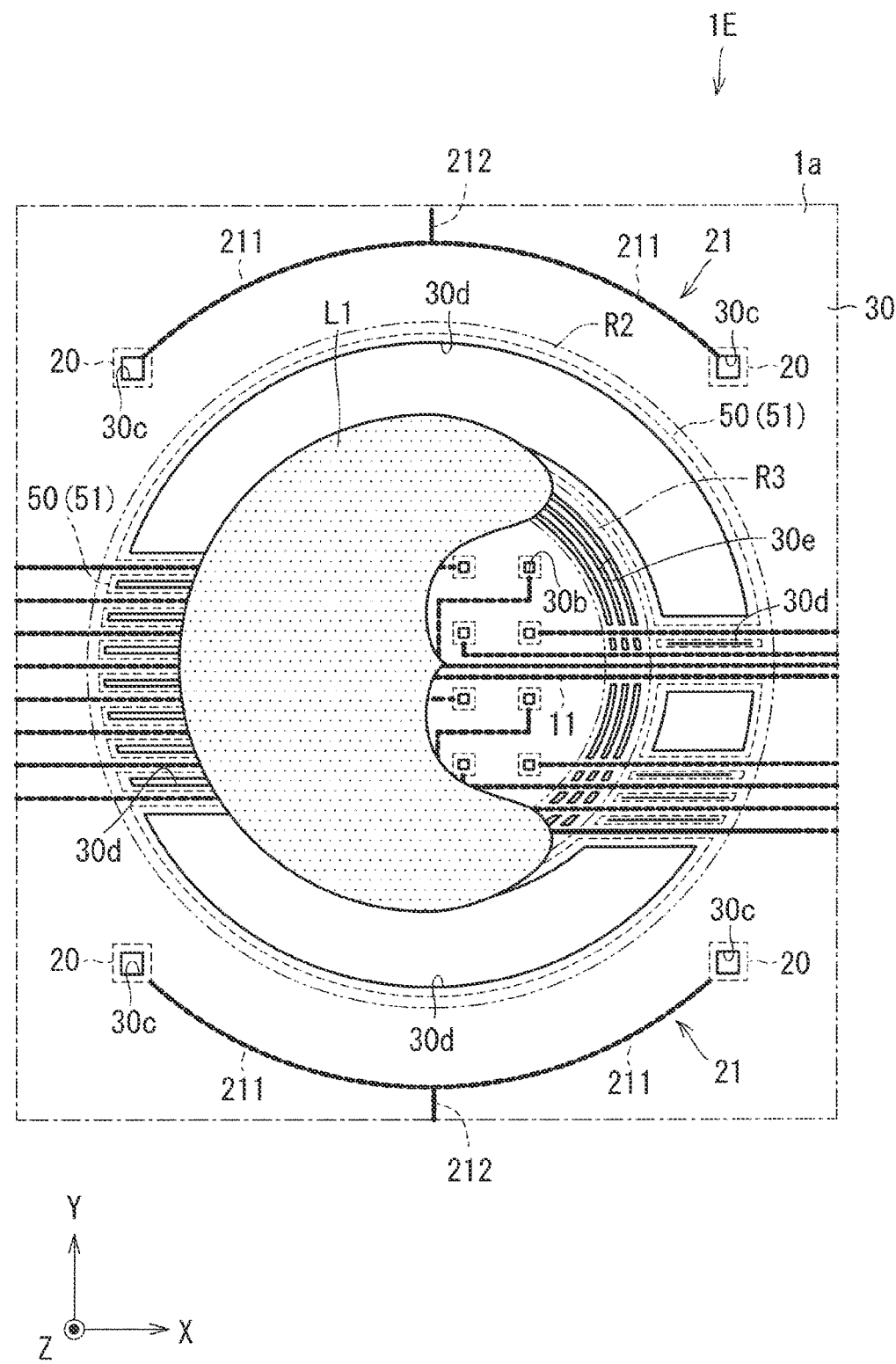
FIG. 17 A diagram schematically illustrating a state of time-series changes in a cell suspension.
Figure 18:
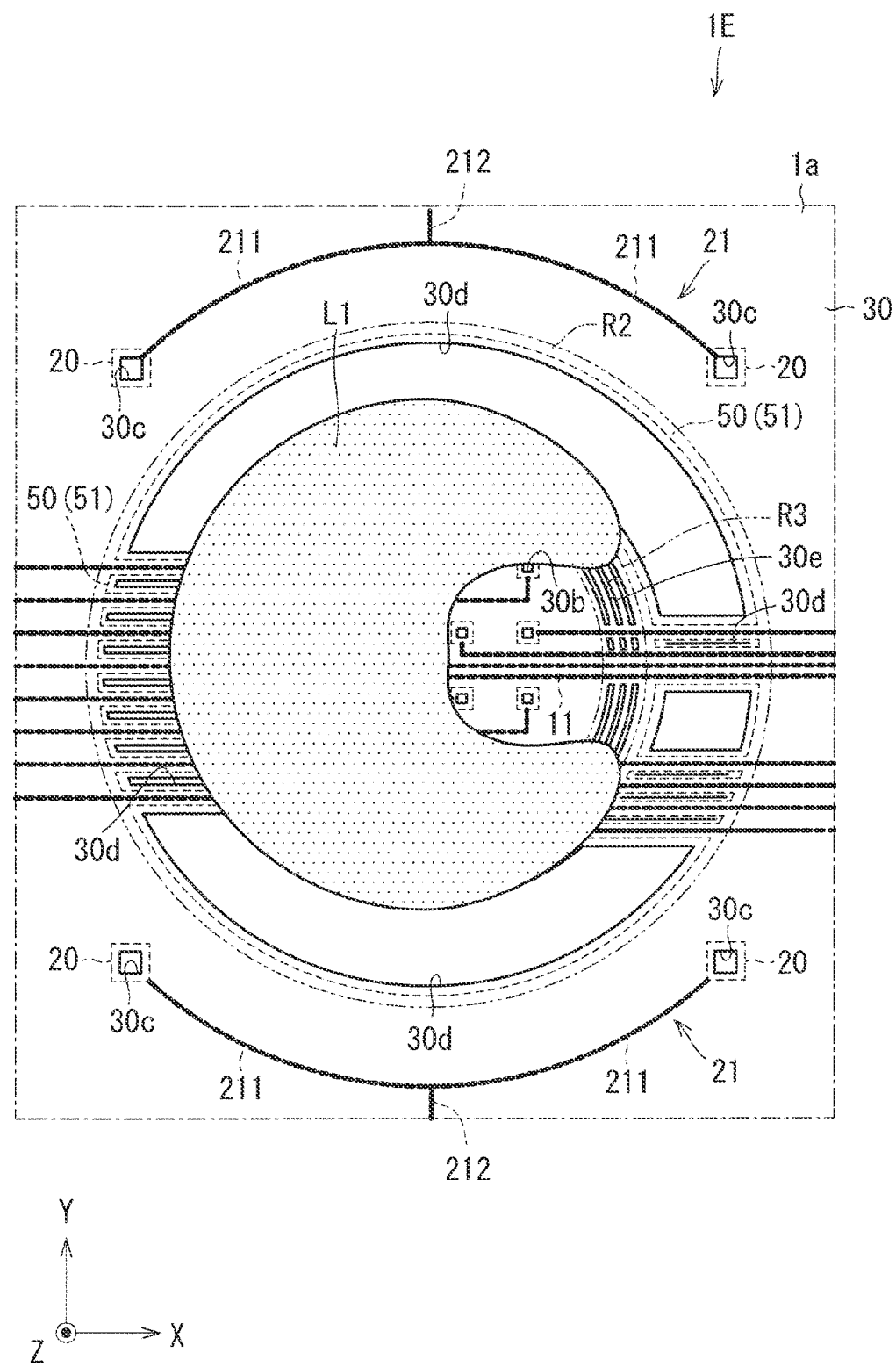
FIG. 18 A diagram schematically illustrating a state of time-series changes in a cell suspension.
Figure 19:
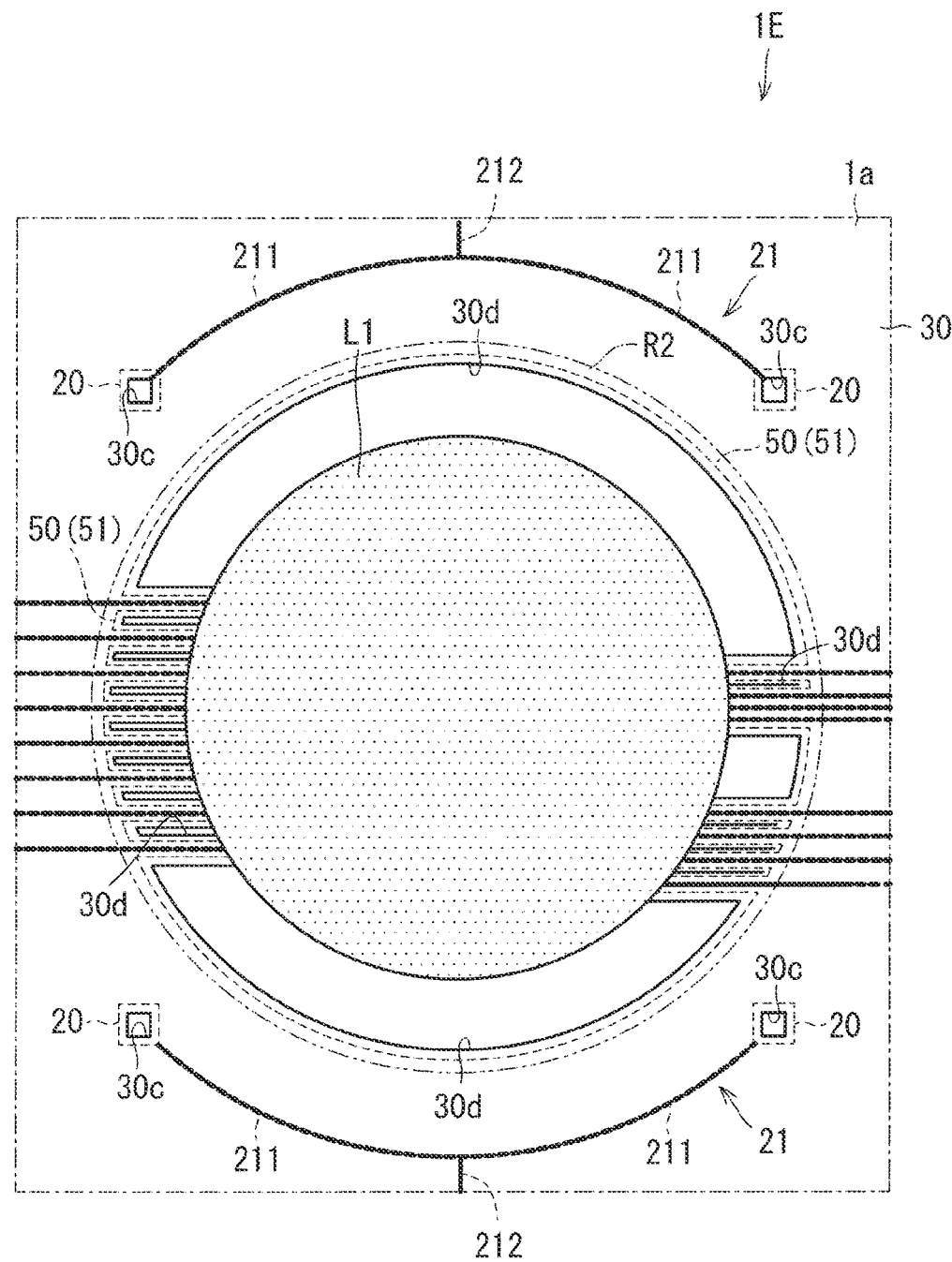
FIG. 19 A diagram schematically illustrating a state of time-series changes in a cell suspension.

FIGS. 17 to 19 are diagrams schematically illustrating an example of a state when the cell suspension L1 is dropped onto the cell potential measurement device 1E. FIGS. 17 to 19 illustrate the time-series changes in the shape of the cell suspension L1 in plan view at the time of dropping. The shape of the cell suspension L1 in plan view changes in the order illustrated in FIGS. 17 to 19. The contact angle in the hydrophilic region R3 of the cell potential measurement device 1E is smaller than the contact angle in the working region R1; therefore, the cell suspension L1 spreads along the circumferential direction of the hydrophilic region R3 to the region on the +X side even if the droplet position of the cell suspension L1 deviates to the −X side (see FIGS. 17 and 18). That is, the cell suspension L1 spreads so as to surround the working region R1 on both the +Y side and the −Y side of the working region R1, merges on the +X side of the working region R1, and the cell suspension L1 in the working region R1 is drawn by the flows on both sides in the Y-axis direction and spreads toward the +X side. This allows the cell suspension L1 to cover the entire working region R1 (see FIG. 19).

As described above, according to the cell potential measurement device 1E, even if the droplet position of the cell suspension L1 deviates from the center of the working region R1, the cell suspension L1 spreads circumferentially along the hydrophilic region R3; therefore the droplet is prone to covering the entire working region R1.

Figure 20:
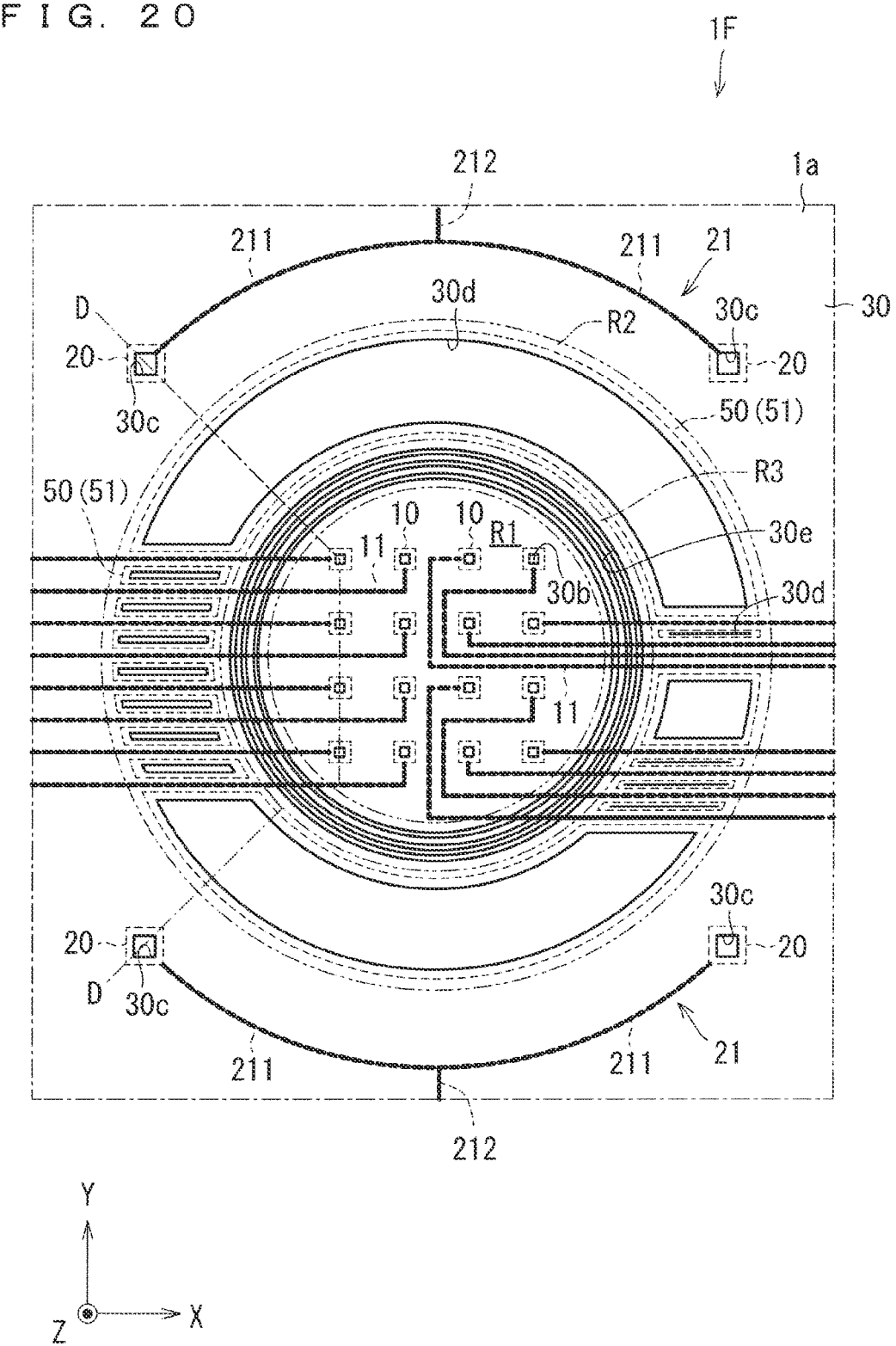
FIG. 20 A cross-sectional view schematically illustrating another configuration example of the cell potential measurement device.

In the above example, the grooves 30e are formed in the regions avoiding directly above the wires 11. However, this is not the only case to be adopted. The grooves 30e may also be provided directly above the wires 11. FIG. 20 is plan view schematically illustrating a configuration example of a cell potential measurement device 1F, and FIG. 21 is a cross-sectional view schematically illustrating the configuration example of the cell potential measurement device 1F. FIG. 21 schematically illustrates a configuration example of in the D-D cross section of FIG. 20.

The cell potential measurement device 1F has the same configuration as the cell potential measurement device 1E except for a shape of the grooves 30e. In the example of FIG. 20, the plurality of substantially circular grooves 30e are formed substantially concentrically. That is, the plurality of grooves 30e are formed over the entire circumference of the working region RE Such grooves 30e are also formed directly above the wires 11. Accordingly, the contact angle in the hydrophilic region R3 as a whole is made small.

However, the wires 11 are required to be covered by the insulating film 30; therefore, the depth of the grooves 30e formed in the insulating film 30 is less than the thickness of the insulating film 30. That is, the grooves 30e of the insulating film 30 are shallower than the openings 30b the openings 30c, and the openings 30d. For example, when the depth of the openings 30b, the openings 30c, and the openings 30d the insulating film 30 is 340 nm, the depth of the openings 30e of the insulating film 30 is set to a lower value smaller than the depth of the openings 30b, the openings 30c, and the openings 30d, which is, for example, 240 nm. In this case, the minimum value of the thickness of the insulating film 30 directly above the wires 11 is 100 nm.

In the cell potential measurement device 1F, forming the grooves 30e and the openings 30b, the openings 30c and the openings 30d by one-time etching is difficult to accomplish. This is because when the insulating film is etched to the depths of the openings 30b, the openings 30c, and the openings 30d, the grooves 30e are also etched to the same depth. Therefore, the etching for the grooves 30a is required to be performed in a step separated from the step for the etching for the openings 30b, the openings 30c, and the openings 30d.

On the other hand, in the cell potential measurement device 1E in which the grooves 30e are formed in the regions avoiding directly above the wires 11, the grooves 30e and the openings 30b, the openings 30c, and the openings 30d can be formed by one-time etching. Therefore, the cell potential measurement device 1E is manufactured in fewer steps than the cell potential measurement device 1F. Accordingly, the manufacturing cost of the cell potential measurement device 1E is more reduced than that of the cell potential measurement device 1F.

In the above example, in the insulating film 30, substantially arc-shape or substantially circular grooves 30e are formed substantially concentrically to form a concavo-convex shape for hydrophilicity; however, this is not the only case to be adopted. For example, in the insulating film 30, dot-shaped (for example, substantially columnar or substantially prismatic) convex portions or dot-shaped concave portions may also be two-dimensionally arranged in the hydrophilic region R3. Alternatively, the hydrophilic region R3 of the insulating film 30 may also have convex portions or concave portions extending radially with respect to the center of the working region R1. In other words, the insulating film 30 may have a concavo-convex shape in the circumferential cross section with respect to the center of the working region R1.

In the above example, although the main surface of the metal film 51 on the +Z side is substantially flat, the metal film 51 may be formed with a concavo-convex shape as in the cell potential measurement device 1C.

Further, in the above example, although the metal film 51 is formed in the same layer as the working electrodes 10, the reference electrodes 20, the wires 11 and the wires 21, the metal film 51 may be formed on the main surface on the +Z side of the insulating film 30 as in the cell potential measurement device 1D.

Further, the metal film 51 is not necessary to be adopted as the hydrophobic film 50, and the hydrophobic film 50 may be formed of a material other than metal.

Further, in the above cell potential measurement device 1E and the cell potential measurement device 1F, the hydrophobic film 50 is provided in the hydrophobic region R2;

however, the hydrophobic film 50 is not necessarily required to be provided. When the hydrophobic film 50 is not provided, the insulating film 30 made of a hydrophilic material may have a fine concavo-convex shape (Cassie Baxter model) in the hydrophobic region R2, and have a rough concavo-convex shape (Wenzel model) rougher than that of the hydrophobic region R2 in the hydrophilic region R3. For example, the pitch of the concave and convex, the width of the convex portions and the width of concave portions in the hydrophobic region R2 are set to less than 1 µm, and the pitch of the concave and convex, the width of the convex portions and the width of the concave portions in the hydrophilic region R3 are set to a larger value than that in the hydrophobic region R2, which is about several µm. As a result, the wettability of the hydrophilic region R3 can be increased while reducing the wettability of the hydrophobic region R2.

While Embodiments have been described above, in the cell potential measurement device, various changes other than those described above can be made without departing from the purpose thereof. Within the scope of the disclosure, present Embodiments can be arbitrarily combined with respective Embodiments, modified any component of respective Embodiments, or can omit any component in respective Embodiments.

EXPLANATION OF REFERENCE SIGNS

1, 1A to 1F cell potential measurement device
10 working electrode
11, 21 wire
20 reference electrode
30 insulating film
50 hydrophobic film
51 metal film
R1 working region
R2 hydrophobic region
R3 hydrophilic region

The invention claimed is:

1. A cell potential measurement device having a measuring plane on which a cell suspension is dropped, the cell potential measurement device comprising:
   a plurality of working electrodes two-dimensionally arranged in a working region of the measuring plane;
   a reference electrode provided outside from the working region of the measuring plane,
   a plurality of wires each drawn from corresponding one of the plurality of working electrodes and the reference electrode; and
   an insulating film covering the plurality of wires, wherein:
   a hydrophobic region, in which a hydrophobic film is disposed, is provided between the working region and the reference electrode of the measuring plane,
   a contact angle in the hydrophobic region is larger than a contact angle in the working region and larger than a contact angle in the insulating film,
   the plurality of wires extends outside the hydrophobic region, and
   the hydrophobic film is a conductive film.

2. The cell potential measurement device according to claim 1, wherein
   the conductive film is formed of a same material as at least any one of that of the plurality of working electrodes or the reference electrode and provided in a same layer as the plurality of working electrodes and the reference electrode so as to be insulated from the plurality of working electrodes and the reference electrode.

3. A cell potential measurement device having a measuring plane on which a cell suspension is dropped, the cell potential measurement device comprising:
   a plurality of working electrodes two-dimensionally arranged in a working region of the measuring plane;
   a reference electrode provided outside from the working region of the measuring plane,
   a plurality of wires each drawn from corresponding one of the plurality of working electrodes and the reference electrode; and
   an insulating film covering the plurality of wires, wherein:
   a hydrophobic region, in which a hydrophobic film is disposed, is provided between the working region and the reference electrode of the measuring plane,
   a contact angle in the hydrophobic region is larger than a contact angle in the working region and larger than a contact angle in the insulating film,
   the plurality of wires extends outside the hydrophobic region, and
   the hydrophobic film has a concavo-convex shape for hydrophobization.

4. The cell potential measurement device according to claim 3, wherein
   the hydrophobic film has the concavo-convex shape in a radial cross section about a center of the working region.

5. A cell potential measurement device having a measuring plane on which a cell suspension is dropped, the cell potential measurement device comprising:
   a plurality of working electrodes two-dimensionally arranged in a working region of the measuring plane;
   a reference electrode provided outside from the working region of the measuring plane;
   a plurality of wires each drawn from corresponding one of the plurality of working electrodes and the reference electrode; and
   an insulating film covering the plurality of wires, wherein:
   a contact angle in a hydrophobic region between the working region and the reference electrode of the measuring plane is larger than a contact angle in the working region,
   the plurality of wires extends outside the hydrophobic region, and
   in the hydrophobic region, the insulating film has a concavo-convex shape for hydrophobization.

6. A cell potential measurement device having a measuring plane on which a cell suspension is dropped, the cell potential measurement device comprising:
   a plurality of working electrodes two-dimensionally arranged in a working region of the measuring plane; and
   a reference electrode provided outside from the working region of the measuring plane, wherein:
   a contact angle in a hydrophobic region between the working region and the reference electrode of the measuring plane is larger than a contact angle in the working region, and
   a contact angle in a hydrophilic region located between the working region and the hydrophobic region and surrounding the working region of the measuring plane is smaller than the contact angle in the working region.

7. The cell potential measurement device according to claim 6, further comprising:
   a plurality of wires each drawn from corresponding one of the plurality of working electrodes and the reference electrode and extending outside the hydrophobic region;

an insulating film covering the plurality of wires and formed of a hydrophilic material; and a hydrophobic film provided in the hydrophobic region, wherein:

a contact angle in the hydrophobic film, which is the contact angle in the hydrophobic region, is larger than a contact angle in the insulating film, and in the hydrophilic region, the insulating film has a concavo-convex shape for hydrophilicity.

8. The cell potential measurement device according to claim 5, wherein the insulating film has the concavo-convex shape in regions avoiding directly above the plurality of wires.

9. The cell potential measurement device according to claim 5, wherein the insulating film has the concavo-convex shape in a radial cross section about a center of the working region.

\* \* \* \* \*